US007521600B2

(12) United States Patent
Gruber et al.

(10) Patent No.: US 7,521,600 B2
(45) Date of Patent: Apr. 21, 2009

(54) REGULATION OF FLAVONOID EXPRESSION IN ALFALFA USING MAIZE REGULATORY GENES

(75) Inventors: Margaret Y. Gruber, Saskatoon (CA); Heather Ray, Saskatoon (CA); Neil Westcott, Saskatoon (CA)

(73) Assignee: Agriculture and Agri - Food Canada (CA)

( * ) Notice: Subject to any disclaimer, the term of this patent is extended or adjusted under 35 U.S.C. 154(b) by 420 days.

(21) Appl. No.: 10/440,045

(22) Filed: May 16, 2003

(65) Prior Publication Data
US 2004/0103456 A1 May 27, 2004

Related U.S. Application Data

(63) Continuation of application No. PCT/CA01/01624, filed on Nov. 16, 2001.

(60) Provisional application No. 60/248,581, filed on Nov. 17, 2000, provisional application No. 60/306,415, filed on Jul. 20, 2001.

(51) Int. Cl.
*C12N 15/29* (2006.01)
*C12N 15/82* (2006.01)
*A01H 5/00* (2006.01)

(52) U.S. Cl. .................. 800/312; 800/282; 800/287

(58) Field of Classification Search .............. 800/282, 800/298, 320.1; 536/23.1, 23.6
See application file for complete search history.

(56) References Cited

U.S. PATENT DOCUMENTS

| 5,900,525 A | 5/1999 | Austin-Phillips et al. .... 800/205 |
| 5,990,385 A | 11/1999 | Vezina et al. ............... 800/278 |

FOREIGN PATENT DOCUMENTS

| WO | WO 91/02059 | * | 2/1991 |
| WO | WO-91/02059 A1 | | 2/1991 |
| WO | WO-93/14211 A1 | | 7/1993 |
| WO | WO-98/07836 A1 | | 2/1998 |
| WO | WO-00/06757 A1 | | 2/2000 |

OTHER PUBLICATIONS

Sharma S. et al. The Plant Journal; 2005, vol. 44, pp. 62-75.*
Ray, H. et al. Plant Physiology, Jul. 2003, vol. 132; pp. 1448-1463.*
Bradley, J. M., et al., "Variation in the ability of the maize Lc regulatory gene to upregulate flavanoid biosynthesis in heterologous systems", *Plant Science*, vol. 140, No. 1, (Jan. 4, 1999), 31-39.
De Majnik, John , et al., "Anthocyanin regulatory gene expression in transgenic white clover can result in an altered patter of pigmentation", *Australian Journal of Plant Physiology*, vol. 27, No. 7, (2000),659-667.
Dixon, R A., et al., "Metabolic engineering: propsects for crop improvement through the genetic manipulation of phenylpropanoid biosynthesis and defense responses—a review", *Gene, Elsevier Science Publishers, Barking*, vol. 179, No. 1, (Nov. 7, 1996),61-71.
Dixon, R A., et al., "Prospects for the Metabolic Engineering of Bioactive Flavanoids and Related Phenylpropanoid Compounds", *Advances in Experimental Medicine and Biology*, vol. 439, (1998),55-66.
Paiva, N L., et al., "Regulation of Osoflavanoid Metabolism in Alfalfa", *Plant Cell, Tissue and Organ Culture, Kluwer Academic Publishers*, vol. 38, No. 2/3, (1994),213-220.

* cited by examiner

*Primary Examiner*—Russell Kallis
(74) *Attorney, Agent, or Firm*—Schwegman, Lundberg & Woessner, P.A.

(57) ABSTRACT

The present invention provides the use of a regulatory gene Lc and encoded protein to alter the biosynthesis and accumulation of flavonoids including anthocyanins and condensed tannins in plants and plant tissues, particularly in alfalfa, white clover, and other forage legumes which are similar in lacking native condensed tannin accumulation in leaves. The identification of the effects of this gene in alfalfa provide a mechanism for altering flavonoid, anthocyanin and condensed tannin production in forage legumes and allows one to alter such levels to produce a variety of benefits in the field of agriculture, animal farming and food technology in general.

20 Claims, 11 Drawing Sheets

GENOTYPE A (90-3) GREEN PHENOTYPE
GENOTYPE B (90-19) RED PHENOTYPE
GENOTYPE C (90-39) SLIGHTLY RED PHENOTYPE
GENOTYPE D (90-40) SLIGHTLY RED PHENOTYPE

REGULATION OF FLAVONOID EXPRESSION IN ALFALFA USING MAIZE REGULATORY GENES

RELATED APPLICATIONS

This application is a continuation under 35 U.S.C. 111(a) of PCT/CA01/01624 filed Nov. 16, 2001 and published in English as WO 02/039809 A3 on May 23, 2002, which claims priority from U.S. Provisional Patent Application No.: 60/248,581, filed on Nov. 17, 2000 and U.S. Provisional Patent Application No.: 60/306,415, filed on Jul. 20, 2001, which applications and publication are incorporated herein by reference.

FIELD OF THE INVENTION

The present invention relates to the use of the Lc gene of maize, and closely related regulatory genes, for altering the biosynthesis and accumulation of flavonoid compounds including anthocyanin and condensed tannin, in alfalfa and other legumes. The present invention further relates to transgenic constructs containing the Lc and allied regulatory genes, for use in the transformation of alfalfa and other legumes, and to transgenic plants containing such constructs.

BACKGROUND OF THE INVENTION

Throughout this application, various references are cited in parentheses to describe more fully the state of the art to which this invention pertains. The disclosure of these references are hereby incorporated by reference into the present disclosure.

Condensed tannins (also called proanthocyanidins) are plant phenolic compounds which are structurally related to the anthocyanins that cause pumple and red colours in flowers. Specifically, condensed tannins are 1,4-linked and 1,6-linked polymers of flavan-4-ols, derived by condensation from several products of the phenylpropanoid/flavonoid pathway (Table 1) (Gruber et al., 1999; Peterson et al., 1999). The biosynthesis of these two classes of compounds, i.e., tannins and anthocyanins, occurs in plants using a set of common genes, after which the pathway diverges and unique genes are required for each class. Many plant species accumulate condensed tannins in their vegetative, floral and seed tissues (Porter 1988). Legumnes are a particularly rich source of these compounds. The legumes sainfoin (*Onobychis viciifolia*) and big trefoil (*Lotus uliginosus*) contain substantial levels of condensed tannins in leaf and other vegetative tissue and in seed coats. With the exception of barley and sorghum seedcoats (Butler 1982; Erdal 1986) and one report in rice (Reddy et al., 1995), the major cereal crops do not express condensed tannins. Several other species such as alfalfa, white clover, *L. japonicus* and the oilseed *Brassica*, only express condensed tannins in seedcoats.

The biological properties of tannins are related to their chemical structure. Their polymeric phenol nature facilitates hydrogen bonding with proteins in preference to other molecules (Hagerman and Butler 1981). The combination of hydroxyl groups (which can easily ionize to form quinone) with the ortho position of hydroxyl groups on ring B (which facilitates metal binding), contribute to their antioxidant properties and their ability to protect from excess sunlight.

Alfalfa (luceme; *Medicago sativa* or *M. falcata*) produces a linear procyanidin (3'4'-OH) condensed tannin polymer in the testa layer of the seedcoat as well as several smaller secreted flavonoids, while the leaves normally produce flavone glycosides instead of tannins (Koupai et al., 1993; Olah and Sherwood, 1971; Saleh et al., 1982). Chalcone synthase (CHS) and dihydroflavonol reductase (DFR) are inconsistently expressed in alfalfa leaves, while the flavanone 3B-hydroxylase (F3H) gene is not detected at all in alfalfa leaves (Charrier et al., 1995; Junghans et al., 1993; Skadauge et al., 1997; Ray and Gruber unpublished).

Leucoanthocyanidin reductases (LARs) comprise the first step committed exclusively to condensed tannins in the flavonoid pathway. LARs are normally expressed only in tannin-containing tissue (Skadhauge, 1996; Koupai-Abyazani et al., 1993; Singh et al., 1997; Joseph et al., 1998). In alfalfa, LCR (3'4'-OH-specific LAR) activity is high only during early seed development, but cannot be detected in leaves (Skadhauge et al., 1997). The flavanone 3B-hydroxylase gene (F3H) and 3'4'-OH-specific leucoanthocyandin reductase gene (LCR) are two functional blocks that prevent alfalfa leaves from accumulating condensed tannins.

Natural and induced mutants affecting condensed tannin or anthocyanin expression have been identified in various crop and forage plant species, including sorghum, barley, pea, *Arabidopsis*, rice and *Lotus japonicus* (Butler et al. 1982; Gruber et al. 1996; Jende-Strid 1993; Koorneef et al. 1982; Koorneef 1991; Jambunathan et al.1986; Reddy et al. 1995). However, no mutations or variants with leaf tannin have been found in alfalfa or related *Medicago* species (Goplen et al., 1980). A somaclonal variant of alfalfa with a small but detectable content of leaf bud flavan-3-ol was recovered (Lees et al., 1992), but tannin could not be extracted from the buds and the trait proved unstable. Somatic hybridization between sainfoin and alfalfa has been used to develop alfalfa-like hybrids with sainfoin DNA, but to date no plants have been recovered with stable leaf tannin contents (Larkin et al., 1998). Alfalfa only accumulates anthocyanins in senescing leaves.

Some forage legume species express condensed tannins in leaves and other vegetative tissues. These include sainfoin, big trefoil (*L. uliginosus*), *L. angustissimus*, all of which express high levels of leaf condensed tannins. Birdsfoot trefoil (*L. corniculatus*) expresses leaf condensed tannin at a moderate level, while the related *L. japonicus* does not express leaf condensed tannin. All of these express condensed tannin in seed coat (Gruber et al., 1999).

The alteration of various intermediates in the phenylpropanoid/flavonoid pathway in certain plants has been demonstrated or suggested to be advantageous for certain uses. For example, certain flavonoids have been suggested to have the ability to inhibit phytopathogens in certain plant species. Flavonoid levels have been manipulated in order to select particular flower colours and patterns. Moreover, increased amounts of condensed tannins in certain forage crops have been found to be useful for decreasing bloat in cattle, improving ruminal protein bypass, reducing intestinal parasites, and reducing sileage degradation by proteolysis.

Researchers have attempted to alter the flavonoid pathway in order to manipulate condensed tannin synthesis in certain plants. Variations in the ability to affect changes in anthocyanin and condensed tannin expression have been observed using the maize C1 gene (myb-like) and myc-like genes constitutively expressed in maize, *Arabidopsis, chrysanthemum*, tomato, petunia, and oats (Lloyd, 1992; Cone et al., 1986; Paz-Arez et al., 1987; Wong et al., 1991; Bradley et al., 1998). For example, the combination of B-Peru (myc-like), and C1 induced anthocyanin production in wheat, barley and oats (Wong et al., 1991). The combination of B-Peru and C1 increased anthocyanin expression only slightly in white clover (maximum 2% of expression level in maize) and in peas (maximum 20% of expression level in maize, except for petal tissue) (de Majnik et al., 1998). B-Perm and C1 were expressed in *Arabidopsis*, and stimulated anthocyanin production in leaves (Lloyd et al., 1992). Lc (myc-like) stimulated anthocyanin expression in *Brassica napus* (Babwah et al., 1998), and in petunia (Bradley et al., 1998), but not in pelargonium or lisianthus (Bradley et al., 1999). A related maize anthocyanin regulatory gene, Sn (myc-like) has been introduced into birdsfoot trefoil (*Lotus conriculatus*) and caused hairy root cultures to become pigmented (Damiani et al., 1998). Unexpectedly, condensed tannins and tannin genes, which are normally elevated in leaves of *Lotus corniculatus*, were either completely suppressed or unaffected in transgenic plants with the Sn gene, while root tannin levels were elevated (Damiani et al., 1999). These authors have recently been able to raise leaf levels with Sn (Damiani, personal communication).

PCT/AU97/00529 is directed to nucleic acids and their encoded polypeptides involved in condensed tannin biosynthesis and their use in regulating the biosynthesis and accumulation of condensed tannins in plants. The nucleic acids are believed to encode leucoanthocyanidin reductases (Lar) of plants.

PCT/GB93/00019 is directed to a method for regulating the expression of one or more anthocyanin pigment genes in a plant. PCT/CA99/00056 is directed to methods and compositions for the alteration of compounds produced by secondary metabolic pathways in plants. Canadian patent application 2,130,800 is directed to a nucleotide sequence encoding flavonoid-3',5'-hydroxylase activity to alter pigment patterns in a transformed plant. PCT/EP99/00419 is directed to the use of certain transcription factor genes for flavonoid biosynthesis in order to manipulate the production of flavonoids other than anthocyains in plants. WO 99/09810 is directed to alfalfa plants having measurable endogenous tannin levels for use as alfalfa forage for improved ruminant health and nutrition and methods of identifying and breeding tannin-expressing alfalfa plants.

Identification of genes which regulate the synthesis of condensed tannins in plants, or of genes regulating the supply of substrate for the condensed tannin branch of the flavonoid pathway may provide a means of developing methods to manipulate the tannin levels of plants advantageously. Such genes and methods could be used, for example, to develop alfalfa with leaves containing moderate condensed tannin levels for improved forage quality, as well as for the development of condensed tannins in canola vegetative tissues to provide insect resistance.

The complexity of the phenylpropanoid/flavonoid pathway often makes it difficult to successfully target specific compounds in the pathway using transgenic constructs and methods to generate stably transformed plants. This is often the case with the prior art. In the present application, the Applicant demonstrates the transformation of alfa with Lc, a regulatory gene of the basic helix-helix-loop or myc class. A spectrum of transgenic plants, ranging from no colour change to plants with dark red/green leaf and stem colouration indicative of anthocyanin accumulation, was obtained using a construct containing the Lc sequence. These results indicate that regulatory genes of this class can stimulate alfalfa leaf flavonoid genes to synthesize substrates all the way down to the branchpoint leading to either anthocyanins or condensed tannins. Thus stably transformed alfalfa plants can be made with improved characteristics for use. Lc has not previously been used to transform alfalfa or other forage legumes as such transformation is not a simple straightforward process.

SUMMARY OF THE INVENTION

The present invention provides methods for alteration of flavonoid, anthocyanin and condensed tannin biosynthesis in a variety of plants, such as alfalfa and other forage legumes using the Lc regulatory gene. This results in transgenic plants with more favourable characteristics such as for example forage quality. In accordance with the present invention is the use of the Lc regulatory gene of maize (*Zea mays*) for the alteration of flavonoid, anthocyanin, and condensed tannin biosynthesis and accumulation in forage legumes, under a suitable promoter.

In one aspect, the Lc regulatory gene is used to transform alfalfa for the alteration of flavonoid, anthocyanin and condensed tannin expression in leaf. The sequence of the Lc gene has been previously determined (Ludwig et al., 1989) and function identified in maize as a limiting regulatory factor controlling expression of structural genes necessary for anthocyanin synthesis. The genomic, cDNA and protein sequence can be obtained in Genbank M26227. GenBank Accession No. M26227 provides the following sequence:

```
cccaaggttc gtggcatatc tgtaggcatc taccccgtct tcgtcgtccg ctcctcacta   (SEQ ID NO:1)

gctaccaaga ggtcgccatt attgccaaca tagagtgtac gtggatgtct atatatatgc ctacttgcac ccatatggca taggcgttcg atccccttag cgcggaggag agctcctccg gttcttctct acccttcgca tggaagttct tgcattgctt cgttgcttct ctagtttctt ccttctacgt ctttccagca tacgcatgcc cctcgtccgc cggttcacga ggcatcgtct gatgatcagt agataataag caatataata ctgatctaga atcgagttgt tgtactcttc gcagataggc gcgtgatggc gctttcagct tcccgagttc agcaggcgga agaactgctg caacgacctg ctgagaggca gctgatgagg agccagcttg ctgcagccgc caggagcatc aactggagct acgccctctt ctggtccatt tcagacactc aaccagggt gctgacgtgg acggacgggt tctacaacgg cgaggtgaag acgcggaaga tctccaactc cgtggagctg acatccgacc agctcgtcat gcagaggagc gaccagctcc gggagctcta cgaggccctc ctgtcgggcg agggcgaccg ccgcgctgcg cctgcgcggc cggccggctc tctgtcgccg gaggacctcg gcgacaccga gtggtactac gtggtctcca tgacctacgc cttccggcca
```

-continued

```
ggccaagggt tgcccggcag gagtttcgcg agcgacgagc atgtctggct gtgcaacgcg
cacctcgccg gcagcaaagc cttcccccgc gcgctcctgg ccaagagcgc gtccattcag
tcaatcctct gcatcccggt tatgggcggc gtgcttgagc ttggtacaac tgacacggtg
ccggaggccc cggacttggt cagccgagca accgcggctt tctgggagcc gcagtgcccg
agctccagcc cgtcaggacg agcaaacgag accggcgagg ccgcagcaga cgacggcacg
tttgcgttcg aggaactcga ccacaataat ggcatggacg acatagaggc gatgaccgcc
gccgggggac acgggcagga ggaggagcta agactaagag aagccgaggc cctgtcagac
gacgcaagcc tggagcacat caccaaggag atcgaggagt tctacagcct gcgacgaa
atggacctgc aggcgctacc actaccgcta gaggacggct ggaccgtgga cgcgtccaat
ttcgaggtcc cctgctcttc cccgcagcca gcgccgcctc cggtggacag ggctaccgct
aacgtcgccg ccgacgcctc aagggcaccc gtctacggct ctcgcgcgac gagtttcatg
gcttggacga ggtcctcgca gcagtcgtcg tgctccgacg acgcggcgcc cgcagcagta
gtgccggcca tcgaggagcc gcagagattg ctgaagaaag tggtggccgg cggcggtgct
tgggagagct gtggcggcgc gacgggagca gcacaggaaa tgagtggcac tggcaccaag
aaccacgtca tgtcggagcg aaagcgacga gagaagctca acgagatgtt cctcgtcctc
aagtcactgc ttccgtccat tcacagggtg aacaaagcgt cgatcctcgc cgaaacgata
gcctacctca aggagcttca gagaagggtg caagagctgg agtccagtag ggaacctgcg
tcgcgcccat ccgaaacgac gacaaggcta ataacaaggc cctcccgtgg caataatgag
agtgtgagga aggaggtctg cgcgggctcc aagaggaaga gcccagagct cggcagagac
gacgtggagc cccccccggt cctcaccatg gacgccggca ccagcaacgt caccgtcacc
gtctcggaca aggacgtgct cctggaggtg cagtgccggt gggaggagct cctgatgacg
cgagtgttcg acgccatcaa gagcctccat ttggacgtcc tctcggttca ggcttcagcg
ccagatggct tcatggggct taagatacga gctcagtttg ctggctccgg tgccgtcgtg
ccctggatga tcagcgaggc tcttcgcaaa gctatgggga gcggtgaag gggcagctgg
aaatttggac atcgacgggc atggaaggct tcatgggatc gaagcaaaga tgtatttctt
gtttctttag ataacagaca tgaatcggac ctttatatca acaattatat gggcatgaat
acttaagact ccagccctta acacgtagaa actcaaaaaa gaagagagga agctaaagac
taagcgtaag gtatatttgg aagtaaatta ttttatagt ttctaagcaa tctcatggtt
tataggaata ctagagtgtt tatggcataa ggtgtttggt tgcattcata aaacctatat
tttcaaagtc atagcattct agataccatg atattttgt aatattggaa actacactcc
aacgcaaagt ttttatgaca tggct.
```

Nucleotides 376-2209 represent the coding sequence and the amino acid sequence encoded by the nucleic acid is (SEQ ID NO:2)
MALSASRVQQAEELLQRPAERQLMRSQLAAAARSINWSYALFWSISDTQPG
VLTWTDGFYNGEVKTRKISNSVELTSDQLVMQRSDQLRELYEALLSGEGDR
RAAPARPAGSLSPEDLGDTEWYYVVSMTYAFRPGQGLPGRSFASDEHVWLC
NAHLAGSKAFPRALLAKSASIQSILCIPVMGGVLELGTTDTVPEAPDLVSR
ATAAFWEPQCPSSSPSGRANETGEAAADDGTFAFEELDHNNGMDDIEAMTA -continued
AGGHGQEEELRLREAEALSDDASLEHITKEIEEFYSLCDEMDLQALPLPLE
DGWTVDASNFEVPCSSPQPAPPPVDRATANVAADASRAPVYGSRATSFMAW
TRSSQQSSCSDDAAPAAVVPAIEEPQRLLKKVVAGGGAWESCGGATGAAQE
MSGTGTKNHVMSERKRREKLNEMFLVLKSLLPSIHRVNKASILAETIAYLK
ELQRRVQELESSREPASRPSETTTRLITRPSRGNNESVRKEVCAGSKRKSP
ELGRDDVERPPVLTMDAGTSNVTVTVSDKDVLLEVQCRWEELLMTRVFDAI
KSLHLDVLSVQASAPDGFMGLKIRAQFAGSGAVVPWMISEALRKAIGKR.

Although generally characterized in maize, its effect in forage legumes, particularly alfalfa, has never been previously demonstrated. Furthermore, due to the complexity of the flavonoid, anthocyanin and condensed tannin biosynthesis pathway, it is often difficult to stably transform different plant species in order to obtain a reproducible effect on the biosynthesis pathway to obtain novel transgenic plants exhibiting the desired genotype and phenotype.

In accordance with an aspect of the present invention is a transgenic alfalfa plant comprising an expressible Lc nucleic acid sequence. In accordance with another aspect of the invention is a transgenic plant, plant tissue or plant cell comprising an expressible nucleic acid sequence encoding a Lc regulatory protein. The nucleic acid sequence of these aspects may be selected from the group consisting of;
  a) a nucleic acid encoding a coding region of the Lc regulatory gene;
  b) a nucleic acid encoding a Lc regulatory gene sequence;
  c) a nucleic acid sequence sharing at least 85% sequence identity with a) or b);
  d) an antisense nucleic acid sequence of a), b) or c);
  e) a nucleic acid which hybridizes under moderate to high stringency with a), b) c) or d);
  f) a nucleic acid complementary to any one of a) to e);
  g) a nucleic acid degeneracy equivalent to any one of a) to f); and
  h) a nucleic acid fragment of any one of a) to g) exhibiting Lc gene biological activity.

In accordance with an aspect of the present invention is a 2.2 kb Lc gene transformed into alfalfa under the control of the CaMV 35S promoter using *Agrobacterium tumefaciens* resulting in a strong red colour indicative of an effect on anthocyanin synthesis.

In accordance with another aspect of the present invention a 2.4 kb Lc gene containing a 200 bp 5'-untranslated region transformed into alfalfa under the control of the CaMV 35S promoter using *Agrobacterium tumefaciens* resulting in a strong red colour indicative of an effect on anthocyanin synthesis.

In accordance with a further aspect of the present invention is a transgenic alfalfa plant expressing anthocyanins and/or condensed tannins.

Because of its regulatory function, Lc can be used in alfalfa either for raising or lowering flavonoid levels in different tissues. These manipulations may be accomplished using plant transformation and sense or antisense constructs of the gene under suitable promoters, depending on the application. Demonstration of Lc function in alfalfa shows that promoters for the structural genes of this pathway are capable of an effective interaction with this regulatory factor. It also shows that Lc, through its effects on the central part of the flavonoid pathway, can supply the substrates needed for condensed tannin synthesis in alfalfa leaf. Lc may stimulate the condensed tan pathway either by direct interaction with all the necessary structural genes for condensed tannin biosynthesis, or following crossing with another transgenic plant which expresses the leucoanthocyanidin reductase (LAR) structural gene or a myb gene.

The Lc gene transformation of alfalfa and other forage legumes may be primarily used for the alteration of condensed tannin synthesis specifically. Furthermore, the present invention also embodies a method for the regulation of flavonoid intermediates required for tannins or other valuable products. In this manner, such transformation provides substrate such that the host plant may be crossed with another plant expressing LAR (whether as a transgene or otherwise), in order to produce or enhance condensed tannin.

In accordance with an aspect of the invention is the use of an isolated nucleic acid comprising a nucleotide sequence encoding a protein which is capable of increasing synthesis of flavonoids or condensed tannins or substrate for condensed, tannins in a plant, preferably a legume and most preferably alfalfa.

In a preferred embodiment, such isolated nucleic acid comprises:
  a) a nucleic acid encoding a coding region of the Lc regulatory gene;
  b) a nucleic acid encoding a Lc regulatory gene sequence;
  c) a nucleic acid sequence sharing at least 85% sequence identity with a) or b);
  d) an antisense nucleic acid sequence of a), b) or c);
  e) a nucleic acid which hybridizes under moderate to high stringency with a), b) c) or d);
  f) a nucleic acid complementary to any one of a) to e);
  g) a nucleic acid degeneracy equivalent to any one of a) to f); and
  h) a nucleic acid fragment of any one of a) to g) exhibiting Lc gene biological activity.

The nucleic acids for use in the invention may include DNA, genomic DNA, cDNA, RNA, mRNA and fragments or portions of the Lc sequence. The isolated nucleic acid encoding Lc may comprise an antisense nucleotide sequence which is capable of decreasing synthesis of condensed tannins or flavonoids in a plant. In a preferred embodiment, such isolated nucleic acid for use in the invention comprises the antisense strand of the Lc gene of maize; the antisense strand of a sequence more than 85% identical to Lc of maize; or a fragment exhibiting Lc gene biological activity, which is antisense to any portion of the Lc gene or has more than 85% homology (sequence identity) with any portion of the Lc gene.

It is understood by one of skill in the art that the Lc nucleic acid sequence for use in the present invention may include isolated nucleic acids that comprise a nucleic acid sequence having at least 70% identity, more preferably at least 75% identity, and still more preferably at least 80%, 85%, 90% and 95%. One skilled in the at would readily comprehend that nucleic acid sequence identity is the percentage of nucleotides in a candidate sequence that are identical with the nucleotides in the subject sequence when aligning the sequences. One skilled in the art would also readily be able to determine the parameters for aligning such sequences and use any appropriate algorithms and computer software in order to achieve the maximal alignment of sequences over their entire length. Furthermore, one skilled in the art would readily comprehend that nucleotides sharing such sequence identity with the Lc sequence are likely to be from other species of grain. The Lc gene may be selected; from a 2.2 kb and a 2.4 kb Lc gene sequence under the control of a suitable promoter.

The invention further includes nucleic acid constructs, vectors and host cells containing the isolated nucleic acids described above for use in transforming legumes, preferably alfalfa, in order to alter flavonoid, anthocyanin, and condensed tannin biosynthesis.

In a preferred embodiment, such legumes include alfalfa (lucerne; *Medicago sativa* or *M. falcata* or hybrids between them); forage legumes similar to alfalfa in having no or low levels of forage condensed tannin expression such that bloat may occur in ruminant animals, including white clover (*Trifolium repens*), red clover (*T. pratense*), alsike clover (*T. hybridum*), sweeteclover (*Melilotus alba* and *M. officinalis*) and subterranean clover (*T. subterranium*). forage legumes differing from alfafa in having substantial or excessive levels of condensed tannin in leaves, such as sainfoin (*Onobrychis*

*viciifolia*), big trefoil (*Lotus uliginosis*), birdsfoot trefoil (*L. corniculatus*), cicer milkvetch (*Astragalus cicer*), sericea (*Lespedeza cuneata*), Kobe lespedeza (*Kummerowia striata*), Korean lespedeza (*K. stipulacea*), trees, shrubs and herbacious plants in general.

The method of the present invention uses the Lc gene sequences in genetic constructs and vectors for transforming plant cells and plant tissues in order to generate transgenic alfalfa plants exhibiting altered levels of flavonoids, anthocyanins or condensed tannins. Such plants may have additional nutritional compounds, altered secondary metabolic profiles, modified taste, texture or appearance, altered profiles of secondary metabolites involved in insect resistance or attraction, disease tolerance, forage quality or other biological processes that are influenced by the phenylpropanoid/flavonoid pathway leading to condensed tannin production.

The invention also includes the use of polynucleotides which age complementary to the disclosed Lc nucleotide sequences, polynucleotides which hybridize to these sequences under moderate to high stringency conditions and polynucleotides which are degeneracy equivalents of these sequences. All such polynucleotides may be used in the method of the present invention.

The term "complementary" is used herein to refer to the sequences of polynucleotides which are capable of forming Watson and Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. Preferably, a "complementary" sequence is a sequence which an A at each position where there is a T on the opposite strand, a T at each S position where there is an A on the opposite strand, a G at each position where there is a C on the opposite strand and a C at each position where there is a G on the opposite strand. Thus one skilled in the art would readily be able to determine such complementary or anticomplementary nucleic acid sequences.

Also as part of the invention are nucleic acid sequences which hybridize to one of the aforementioned nucleic acid sequences under stringent conditions. "Stringent conditions" as used herein refers to parameters with which the art is familiar and such parameters are discussed, for example, in the latest editions of Molecular Cloning: A Laboratory Manual, J. Sambrook, et al., eds., Cold Spring Harbor Laboratory Press, Cold Spring Harbor, N.Y., or Current Protocols in Molecular Biology, F. M. Ausubel, et al., eds., John Wiley & Sons Inc., New York.

It is noted that the nucleic acid molecules described herein represent a preferred embodiment of the invention. The invention also encompasses degenerate nucleic acids that differ from the aforementioned sequences. Due to degeneracy in the genetic code, variations in the DNA sequence will result in translation of identical peptides. It is thus understood that numerous choices of nucleotides may be made that will lead to a sequence capable of directing production of the peptides or functional analogs thereof of the present invention. As a result, degenerative nucleotide substitutions are included in the scope of the invention.

In accordance with another embodiment, the invention provides alterations of the isolated Lc sequences that may be used, for example, for expression and functional studies of the encoded protein in alfalfa, other forage legumes. The Lc DNA and cDNA sequences can be altered using procedures such as restriction enzyme digestion, DNA polymerase fill-in, exo-nuclease deletion, terminal deoxynucleotide transferase extension, ligation of synthetic or cloned DNA sequences and site-directed in vitro mutagenesis, including site-directed sequence alteration using specific oligonucleotides together with PCR. The Lc DNA and cDNA sequence may also be altered using site-specific recombination for example.

For protein expression, eukaryotic and prokaryotic expression systems may be generated in which the Lc gene sequence is introduced into a plasmid or other vector which is then introduced into living plant cells. Constructs in which the Lc cDNA sequence containing the entire open reading frame is inserted in the correct orientation into an expression plasmid may be used for protein expression. Alternatively, portions of the sequence may be inserted. Prokaryotic and eukaryotic expression systems allow various important functional domains of the protein to be recovered as fusion proteins and used for binding, structural and functional studies and also for the generation of appropriate antibodies Typical expression vectors contain promoters that direct the synthesis of large amounts of mRNA corresponding to the gene. As used herein, a suitable promoter may be for example but not limited to a 35S promoter, a nos promoter, small subunit rubisco promoter, light-induced promoters, leaf specific promoters, vegetative promoters or any other promoters which are expressed in the desired plant tissue in accordance with the selected application. Plant cells and tissues include but are not limited to leaf, stem, flower, root, developing seed, mature seed and seedling. Typical expression vectors may also include sequences allowing autonomous replication within the host organism, sequences that encode genetic traits that allow cells containing the vectors to be selected, and sequences that increase the efficiency with which the mRNA is translated. Stable long-term vectors may be maintained as freely replicating entities by using regulatory elements of viruses. Cell lines may also be produced which have integrated the vector into the genomic DNA and in this manner the gene product is produced on a continuous basis.

In accordance with a further embodiment, the invention provides a transgenic plant or plant cell transformed with a nucleic acid comprising a nucleotide sequence encoding the amino acid sequence of Lc and wherein the nucleotide sequence is expressed. In a preferred embodiment, the plant or plant cell is alfalfa transformed with and expresses a nucleic acid comprising the nucleotide sequence of Lc. The plant or plant cell may be a monocot or a dicot. Preferably, the plant or plant cell is selected from the group consisting of a legume, for ample alfalfa The invention further provides a method for inducing or increasing condensed tannin synthesis in an alfalfa plant comprising:

transforming an alfalfa plant with a nucleic acid sequence selected from the group consisting of;
  a) a nucleic acid encoding a coding region of the Lc regulatory gene;
  b) a nucleic acid coding for a Lc regulatory gene sequence;
  c) a nucleic acid sequence sharing at least 85% sequence identity with a) or b);
  d) an antisense nucleic acid sequence of a), b) or c);
  e) a nucleic acid which hybridizes under moderate to high stringency with a), b) c) or d);
  f) a nucleic acid complementary to any one of a) to e);
  g) a nucleic acid degeneracy equivalent to any one of a) to f);
  h) a nucleic acid fragment exhibiting Lc gene biological activity of any one of a) to g); and growing said plant The invention further provides a method for suppressing or reducing condensed tannin synthesis in an alfalfa plant comprising:

transforming an alfalfa plant with an isolated nucleic acid comprising the antisense strand of a nucleotide sequence encoding the amino acid sequence of Lc, under the control of a suitable promoter.

The invention further provides a method for regulating production of flavonoid and flavonoid intermediates in an alfalfa plant comprising:

transforming an alfalfa plant with an isolated nucleic acid selected from the group consisting of:
a) a nucleic acid encoding a coding region of the Lc regulatory gene;
b) a nucleic acid encoding Lc regulatory gene sequence;
c) a nucleic acid sequence sharing at least 85% sequence identity with a) or b);
d) an antisense nucleic acid sequence of a), b) or c);
e) a nucleic acid which hybridizes under moderate to high stringency with a), b) c) or d);
f) a nucleic acid complementary to any one of a) to e);
g) a nucleic acid degeneracy equivalent to any one of a) to f); and
h) a nucleic acid fragment of any one of a) to g) exhibiting Lc gene biological activity.

The above methods may be used to increase or induce, suppress or reduce condensed tannin synthesis in a wide variety of plants, most preferably forage legumes such as alfalfa.

According to a further aspect of the invention is a method for producing a transgenic plant, plant tissue or plant cell exhibiting altered levels of flavonoids, anthocyanins or condensed tannins, said method comprising the steps of;

transforming a legume plant, plant tissue or plant cell with a nucleic acid sequence selected from the group consisting of:
a) a nucleic acid encoding a coding region of the Lc regulatory gene;
b) a nucleic acid encoding a Lc regulatory gene sequence;
c) a nucleic acid sequence sharing at least 85% sequence identity with a) or b);
d) an antisense nucleic acid sequence of a), b) or c);
e) a nucleic acid which hybridizes under moderate to high stringency with a), b) c) or d);
f) a nucleic acid complementary to any one of a) to e);
g) a nucleic acid degeneracy equivalent to any one of a) to f); and
h) a nucleic acid fragment of any one of a) to g) exhibiting Lc gene biological activity.

According to a further embodiment of the invention is the use of the Lc gene in a plant, plant cell or tissue, to increase condensed tannin content for improving forage quality and as a result, improving animal health, carcass weight gain, milk and wool production and decreasing bloat in animals. Such plants include but are not limited to alfalfa (lucerne; *Medicago sativa* and *M. falcata* and hybrids between them), white clover (*Trifolium repens*), red clover (*T. pratense*), alsike clover (*T. hybridum*), sweetclover (*Melilotus alba* and *M. officinalis*) and subterranean clover (*P. subterranium*).

In accordance with a further aspect of the present invention is the use of a genetic construct comprising the Lc nucleotide sequence in a sense or antisense orientation under the control of a suitable promoter which is capable of expression in a designated plant part for transformation of alfalfa and other forage legumes, for increasing tolerance or resistance to infection by fungi, viruses and/or bacteria; and, for increasing tolerance or resistance to disease, insects, nematodes, and other pest species.

According to yet another aspect of the invention is the use of the Lc nucleotide sequence in alfalfa and forage legumes, in sense or antisense orientation, to affect condensed tannin content for nutraceutical use; and, to affect condensed tannin content for the purposes of altering flavour, colour and/or astringency in plants used directly or processed for food.

BRIEF DESCRIPTION OF THE DRAWINGS

The present invention will be further understood from the following description with reference to the Figures, in which:

FIG. 1 are Northern and Southern blots showing family series 90 of Lc-transformed alfalfa.

Panel A. Northern blot analysis of three flavonoid genes in leaves of untransformed alfalfa (*Medicago sativa* cv. Beaver) and leaf-tannin-accumulating legume species. F3H and DFR do not appear in untransformed alfalfa leaves, while CHS is reduced.

Panel B. Northern blot analysis of one Lc-genotype (88-19) from family 88 containing a 2.4 Kb transgene grown for five days under cold (4° C.) and variable light conditions. The red leaf and stem colour disappeared when the plants were returned to room temperature.

Panel C. Northern blot analysis of four Lc,-genotypes (family 90, 2.2 kb transgene) grown five days under cold and variable light conditions. L designates an RNA ladder. The red leaf and stem colour disappeared when the plants were placed at room temperature.

Panel D. Anthocyanin extracted from 1 g macerated leaf tissue from four family 90 genotypes containing the 2.2 kb Lc gene exposed to the high stress of natural daylight for 4 days (750 µE). The red phenotype disappeared when plants were returned to continuous growth in the milder conditions of a greenhouse (500 uE, 20° C.).

Panel E. Anthocyanin extracted from 1 g macerated leaf tissue from transgenic genotypes family 88 containing the 2.4 kb Lc gene and three non-transformed breeding lines exposed to the high stress of natural daylight for 9 h per day for 4 days (750 µE). The phenotype disappeared when plants were returned to continuous growth under milder conditions in a greenhouse. Genotype A01 is the untransformed parent genotype used to generate Lc-transgenic plants.

Panel F. Dark red-purple phenotype of Lc-genotype 88-19 (2.4 kb transgene) and untransformed parent genotype A01 after exposure to cold or natural daylight. The red phenotype disappeared when plants were returned to continuous growth under mild greenhouse conditions.

Panel G. Closeup of leaves and stems of Lc-genotype 88-19 (2.4 transgene) and untransformed parent genotype A01 after exposure to cold or natural daylight.

Panel H. Light micrograph illustrating the accumulation of anthocyanin in mesophyll cells of Lc-genotype 88-19 (2.4 transgene) and untransformed parent genotype A01 after exposure to cold or natural daylight.

Figures 3A, 3B:
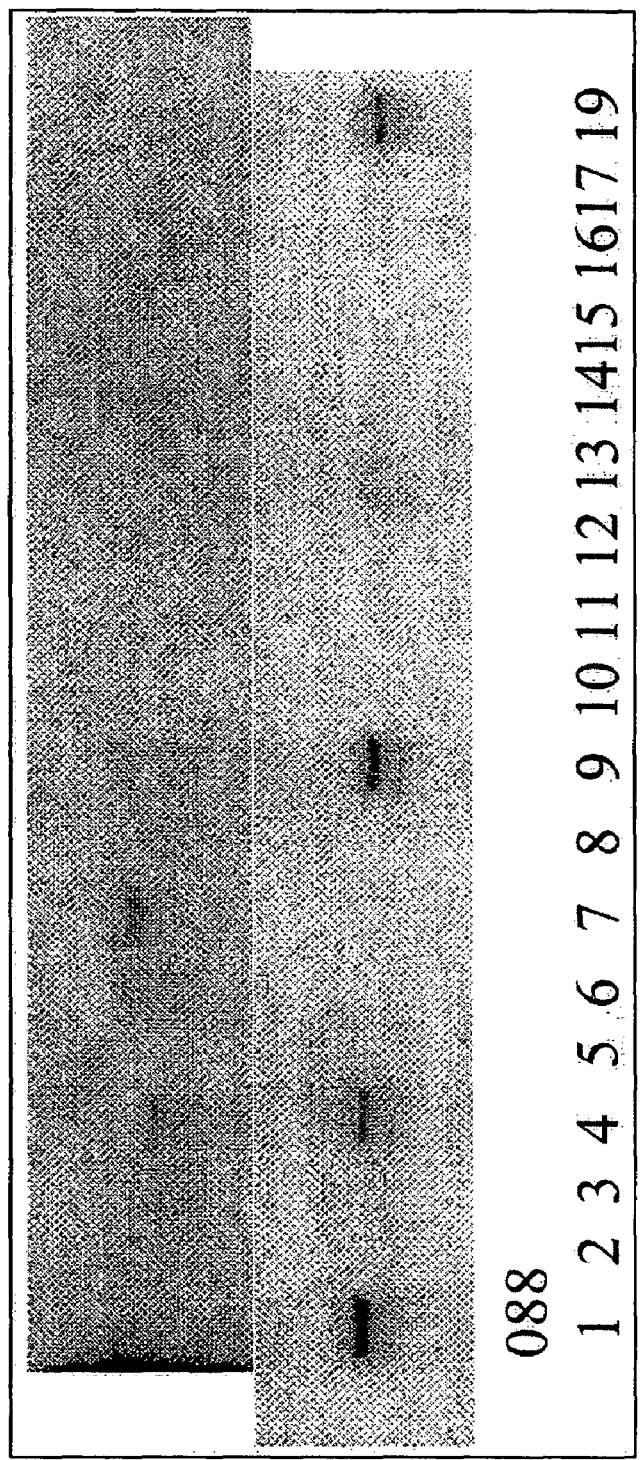
Figures 3C, 3D:
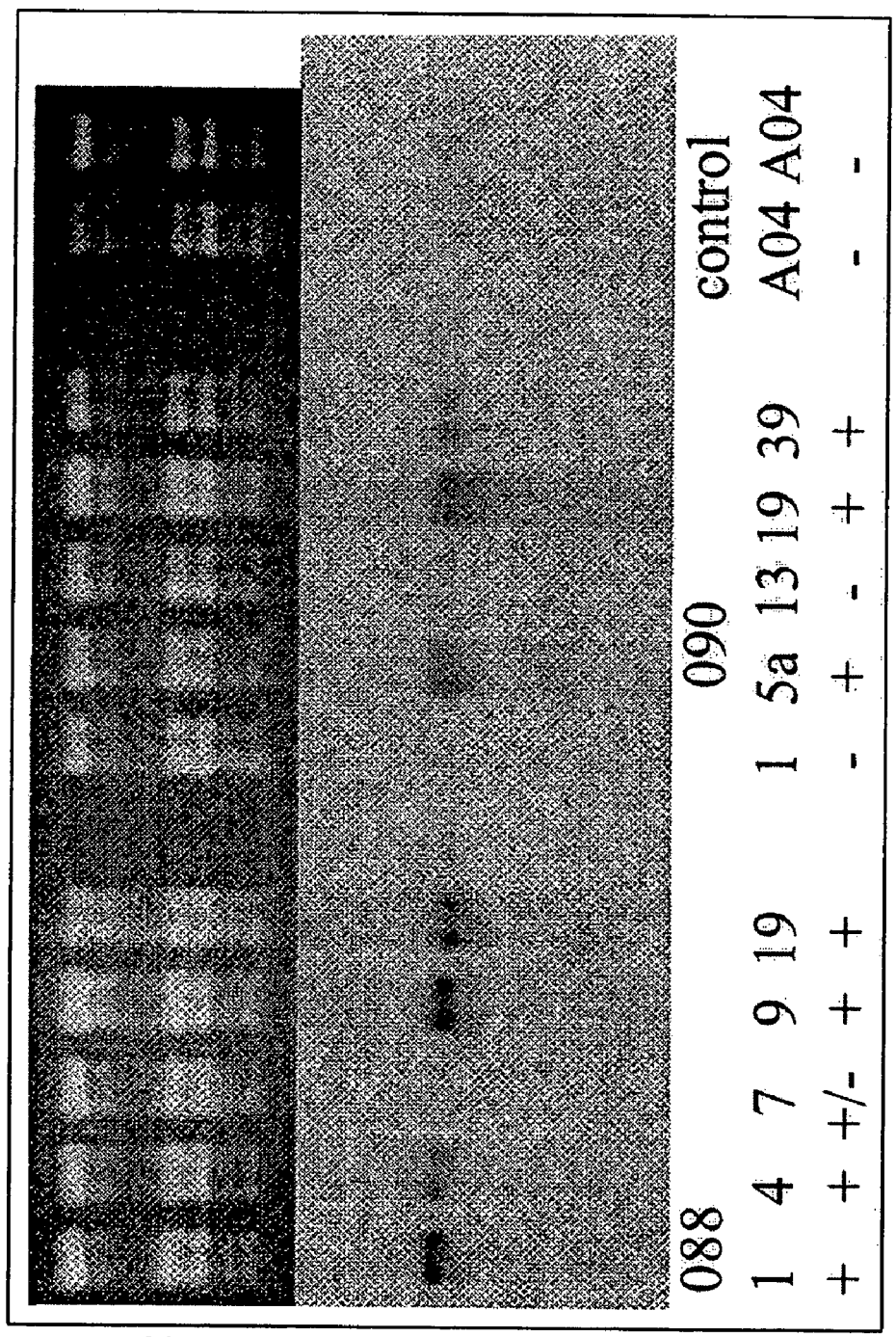
Figures 3E, 3F:
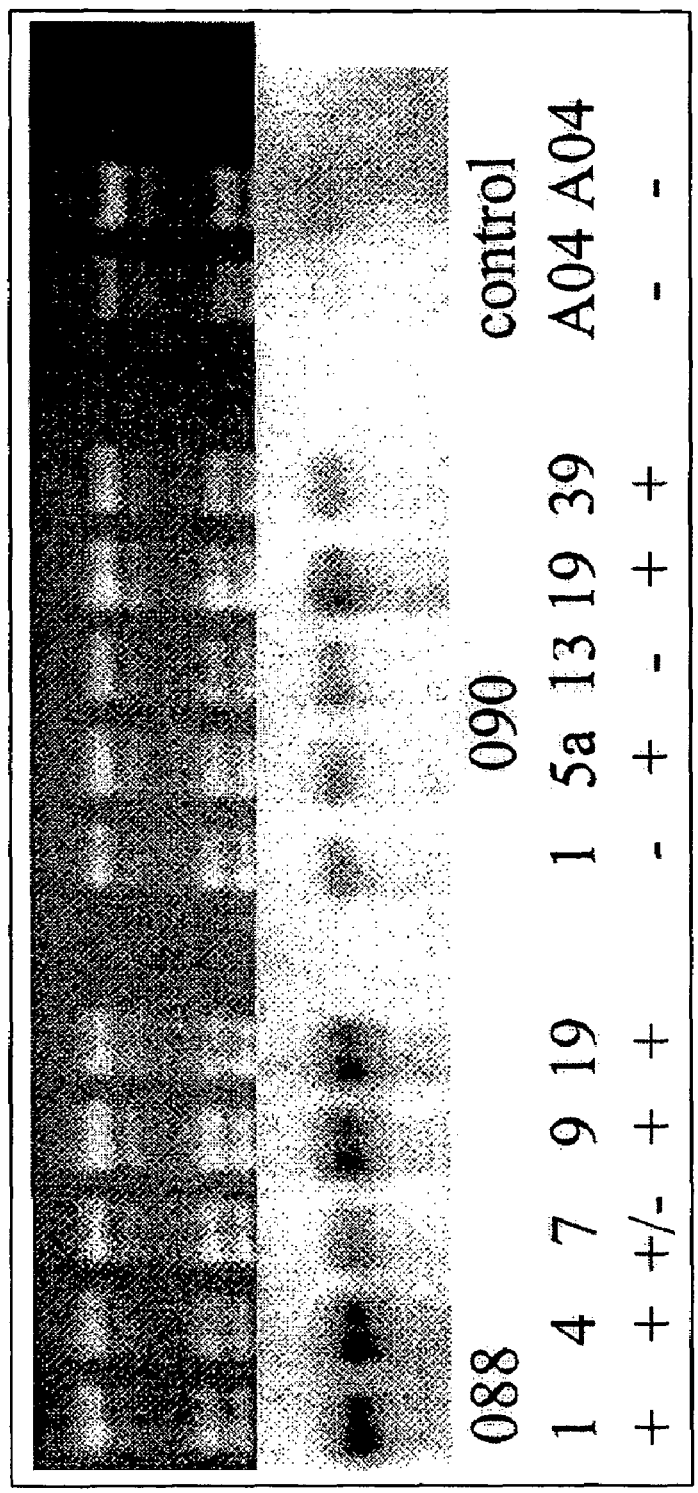

FIG. 3 are southern and northern blots showing the presence of Lc (2.4 kb) in transgenic alfalfa family 88 and analysis of field-grown 88 and 90 genotypes.

Panel A. Southern blot probed with the Lc gene showing a range of trasgenic genotypes in family 88.

Panel B. Northern blot of young leaves from greenhouse-grown plants of family 88 in which no red colour could be observed.

Panel C-F. Gene expression study on field grown leaf material from five alfalfa plants from each transgenic family. Genotype numbers for each of the lane designations at the bottom of F apply similarly to panels C-F. Approximate levels of anthocyanin extracted from leaves of the field-grown genotypes are indicated by +/− symbols.

Panel C. RNA gel blotted in D indicating RNA quality.

Panel D. Northern blot of C probed with Lc.

Panel E. RNA gel blotted in F indicating RNA quality.

Panel F. Northern blot probed with alfalfa CHS gene.

Blots were also hybridized with probes for alfalfa F3H and DFR under the same conditions, but no expression was evident for these genes. Transient expression of F3H and DFR RNA during initial periods of adaptation to natural light conditions may suffice to maintain anthocyanin levels.

In the drawings, preferred embodiments of the invention are illustrated by way of example. It is to be expressly understood that the description and drawings are for the purpose of illustration and as an aid to understanding, and are not intended as a definition of the limits of the invention.

DETAILED DESCRIPTION OF THE INVENTION

The present invention demonstrates the use of the Lc regulatory gene of maize to increase or decrease anthocyanin and/or condensed tannin levels in plants, particularly in alfalfa and forage legumes which are similar in lacking condensed tannins in leaves, or alternatively in forage legumes which have excessive levels of condensed tannins in leaves. Thus the invention provides methods for use of the Lc gene of maize, and closely related regulatory genes, for altering the biosynthesis and accumulation of flavonoid compounds including anthocyanin and condensed tannin, in alfalfa and other legumes. The present invention further provides transgenic constructs containing the Lc and allied regulatory genes, for use in the transformation of alfalfa and other legumes, and to novel transgenic plants containing such constructs.

Lc is a maize (*Zea mays*) regulatory factor of the myc or basic helix-loop helix class. Its sequence is known (Genbank M26227; Ludwig et al., 1989). It has not previously been identified as affecting anthocyanin levels in a legume. It has a high degree of homology to the maize genes B-Peru and lower degrees of homology to numerous plant genes containing the basic helix-loop-helix motif. The expression patterns and effects of few of this numerous class have been determined, but myc genes have been implicated in anthocyanin biosynthesis accumulation in maize and, when transformed into other plants, in *Arabidopsis* (Lloyd et al., 1997), *Brassica napus* (Babwah et al., 1998) and petunia (Bradley et al., 1998). Their involvement in other facets of plant development, such as cell shape, has been identified (Lloyd et al., 1997; Babwah et al., 1998). While myc genes may have been previously suggested to have utility in altering condensed tannin expression in alfalfa and other forage legumes, any previous attempts to show alterations in flavonoid products in alfalfa by the use of a myc gene have been unsuccessful.

The present invention is the first to establish that the Lc gene, when transformed into alfalfa, is capable of effective interaction with alfalfa genes to stimulate the parts of the flavonoid pathway in common between anthocyanins and condensed tannins, and to stimulate the anthocyanin-specific branch of this pathway. While such transformation may also directly affect structural gene expression of the condensed tannin-specific branch of the pathway, the reduction of flavones and the accumulation of anthocyanin clearly demonstrates that Lc can provide leucoanthocyanidin substrate for the LAR gene, the first structural gene of the condensed tannin-specific branch of the flavonoid pathway (Table 1). In combination with the LCR structural gene in a double-transgenic plant, this may permit leaf expression of condensed tannins.

The 2.2 kb Lc gene was placed under the control of the CaMV 35S promoter, which is expressed in leaf and in additional tissues of maize, and transformed into alfalfa using *Agrobacterium tumefaciens* (McKersie et al., 1996). This experiment generated Family 90 of Lc-transgenic plants indicated in FIGS. 1, 2 and 3. A second gene construct was also used to transform alfalfa in order to stimulate production of the flavonoid pathway. The second construct encoded a 2.4 kb Lc gene containing a 200 bp 5'-untranslated region and generated Family 88 of Lc-transgenic plants indicated in FIGS. 2, and 3. The 200 bp region has been shown to function as a post-transcriptional repressor in maize and Arabidopsis (Lloyd et al., 1992). Both constructs were subcloned in a similar manner and expressed by a single CaMV35S promoter. In addition, alfalfa was transformed with a homologize from maize, B-Peru under the control of an enhanced CaMV35S promoter in order to determine the specificity of the gene sequence required to function in alfalfa. B-Peru has been shown to stimulate anthocyanin production in white clover (de Majnik et al., 1998). The transformation resulted in a strong red colour in leaves and stems of transgenic alfalfa, the intensity of which was affected by certain environmental factors, i.e. light and temperature conditions. This red colour is produced by anthocyanins, an alternative end point in the lower flavonoid pathway leading to condensed tannins (Table 1). Normally, anthocyanins and condensed tannins do not accumulate in detectable quantities in non-transformed alfalfa leaves, while flavones synthesized by early genes accumulate as a major flavonoid product. In addition, the F3H gene is normally not expressed and LAR activity is absent in alfalfa leaves, while CHS and DFR are inconsistently expressed in this tissue (Charrier et al., 1995; Junghans et al., 1993; Skadhauge et al., 1997) (FIG. 2A). This pattern is indicative of blocked expression in intermediate and late flavonoid genes in alfalfa forage and contrasts with the strong gene expression noted in tannin-accumulating leaf tissues of several legume species (FIG. 2A).

Figure 1A:
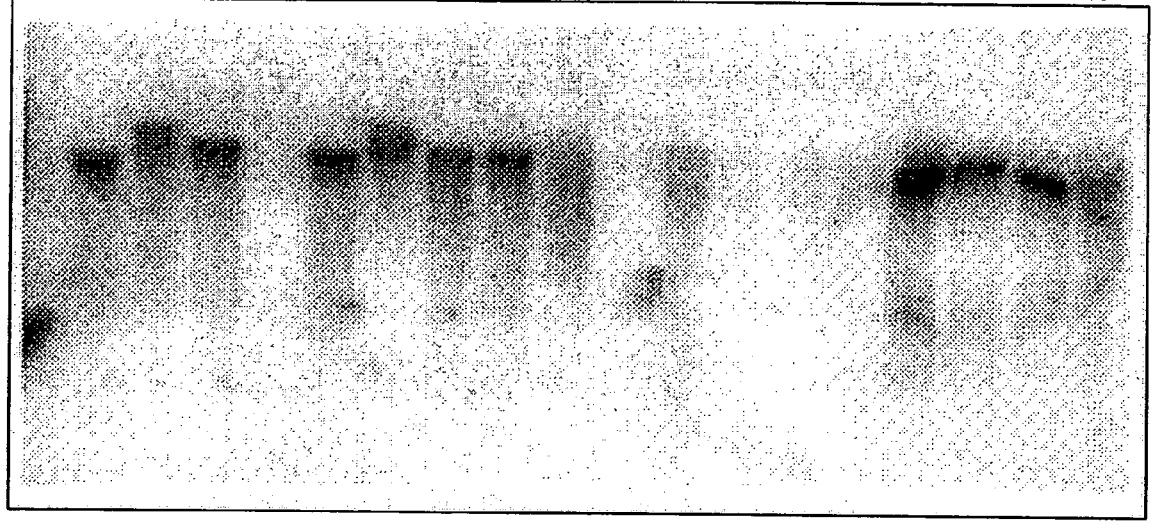
FIGS. 1A, 1B are Southern blots showing the presence of the 2.2 kb Lc gene of maize in this family of trangenic alfalfa.
Figure 1B:
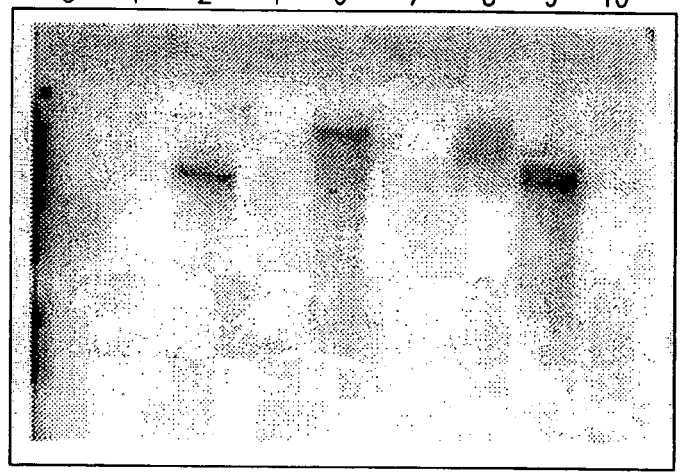
Figure 1C:
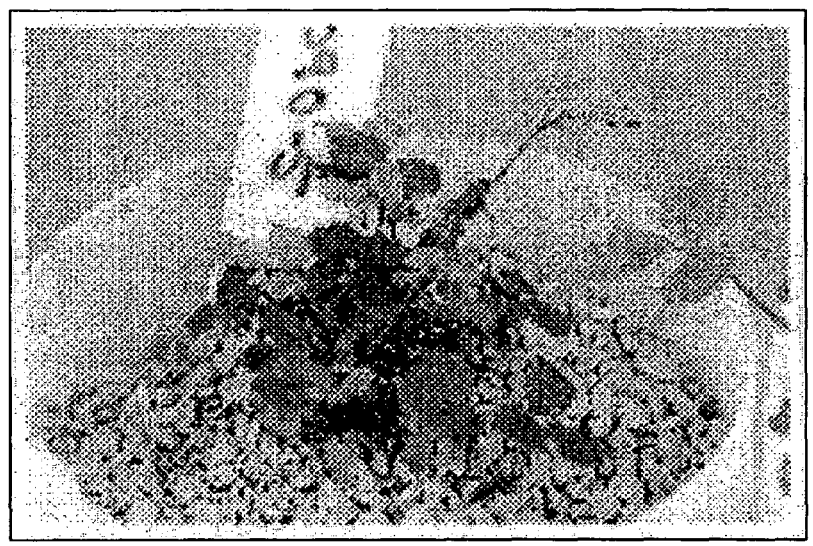
FIG. 1C is a photograph of a young alfalfa plant transformed with the 2.2 kb Lc gene illustrating red phenotype.
Figure 1D:
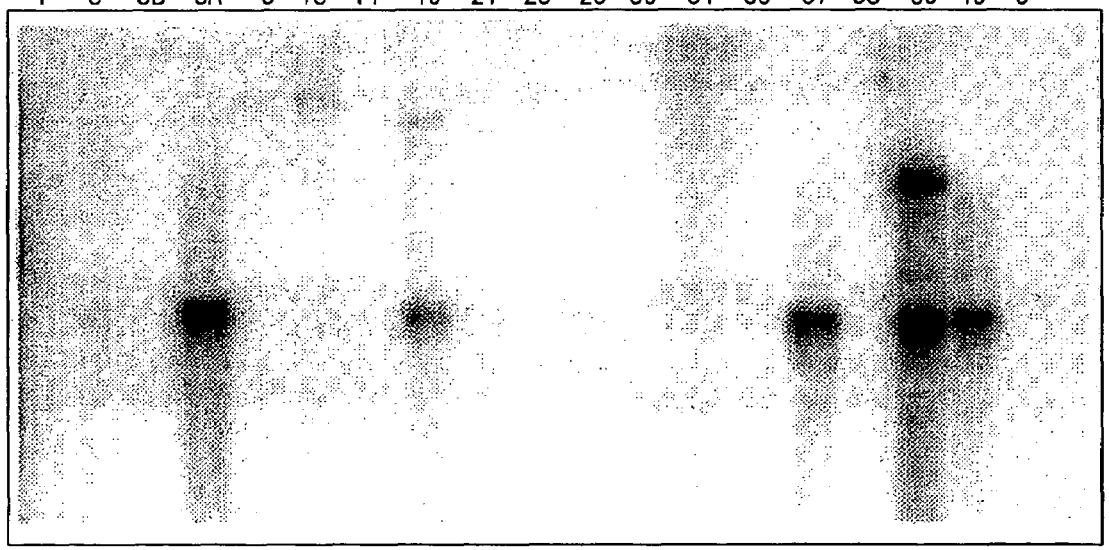
FIGS. 1D, 1E are Northern blots showing expression of Lc in young leaf tissue of the same family of plants probed with Lc.
Figure 1E:
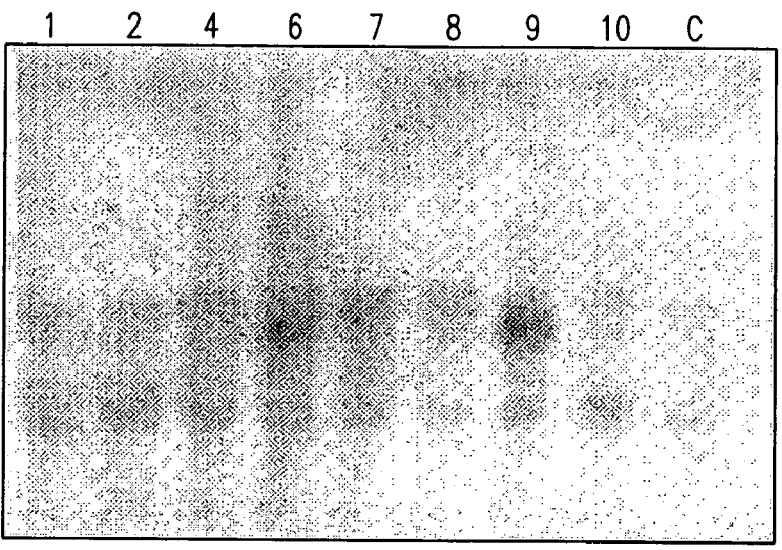
Figure 1F:
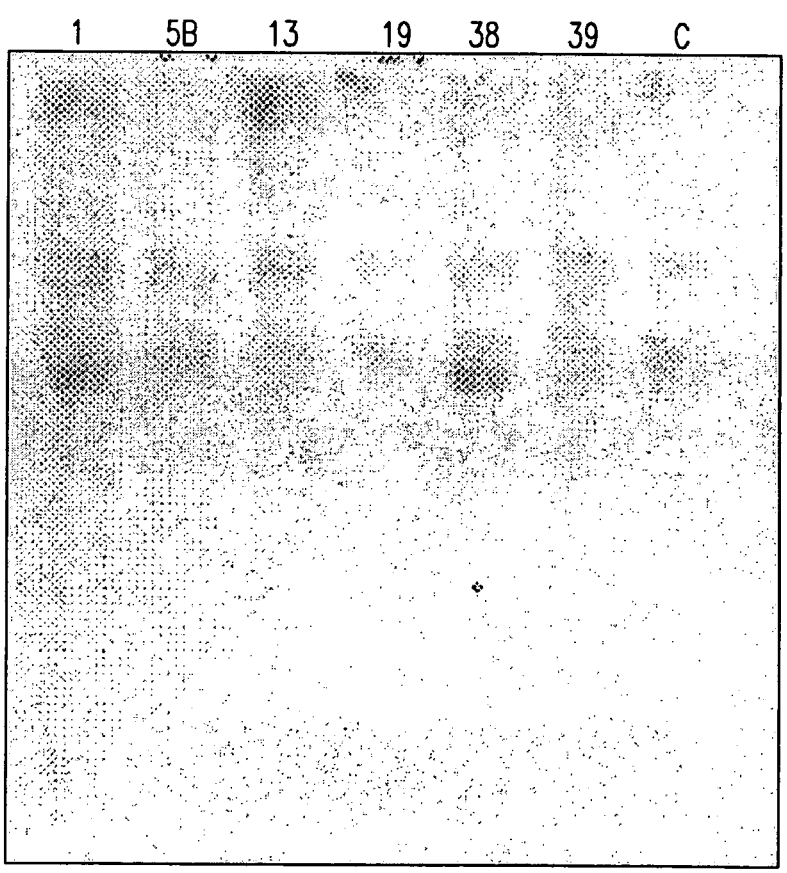
FIG. 1F is a Northern blot showing expression of GHS in young leaf tissue of a subset of transgenic alfalfa, probed with alfalfa CHS. The plants used for Northerns in panels D, E and F were grown under normal greenhouse conditions. C indicates a non-transformed control plant.
Figure 2A:
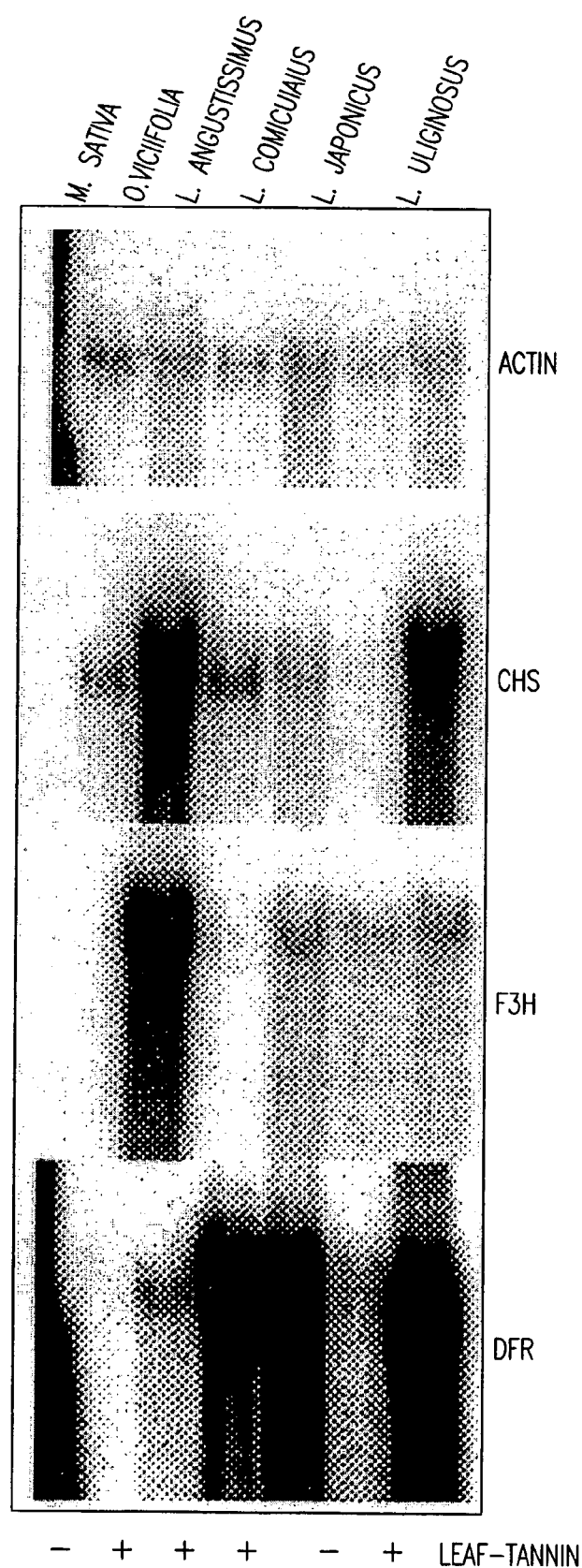
FIG. 2 are Northern blots and photographs of plants showing flavonoid gene expression and product accumulation patterns in Lc-transgenic alfalfa under cold temperatures or natural daylight.
Figure 2B:
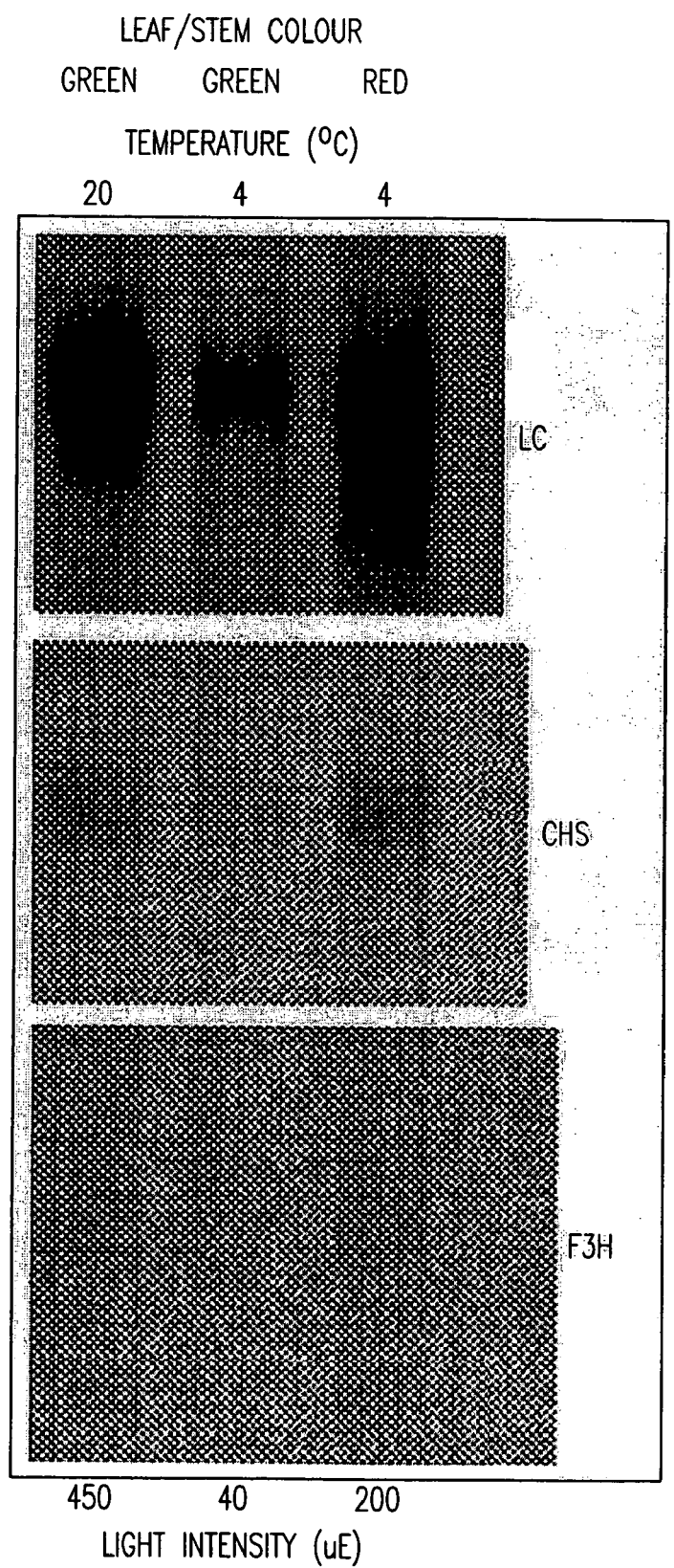
Figure 2C:
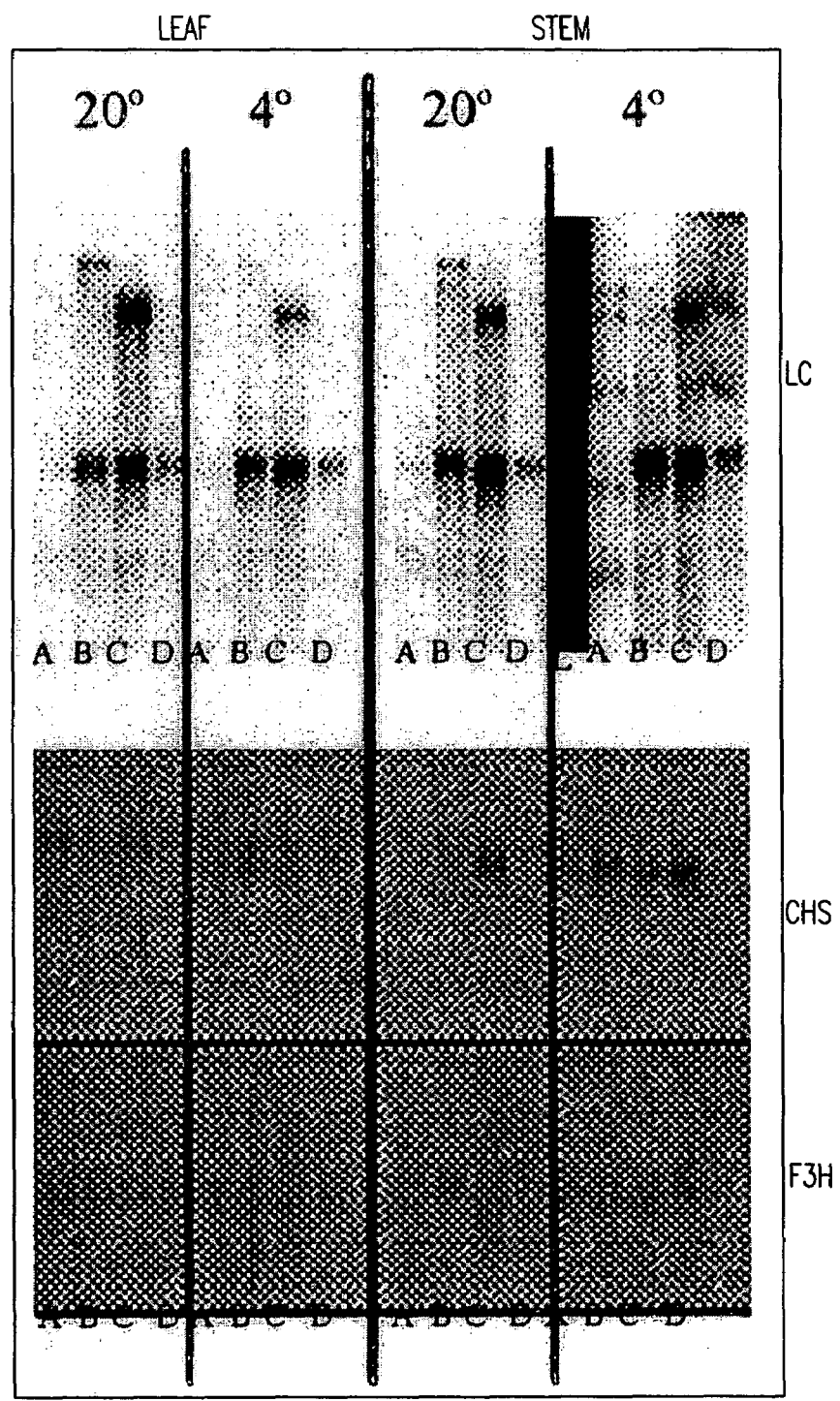
Figure 2D:
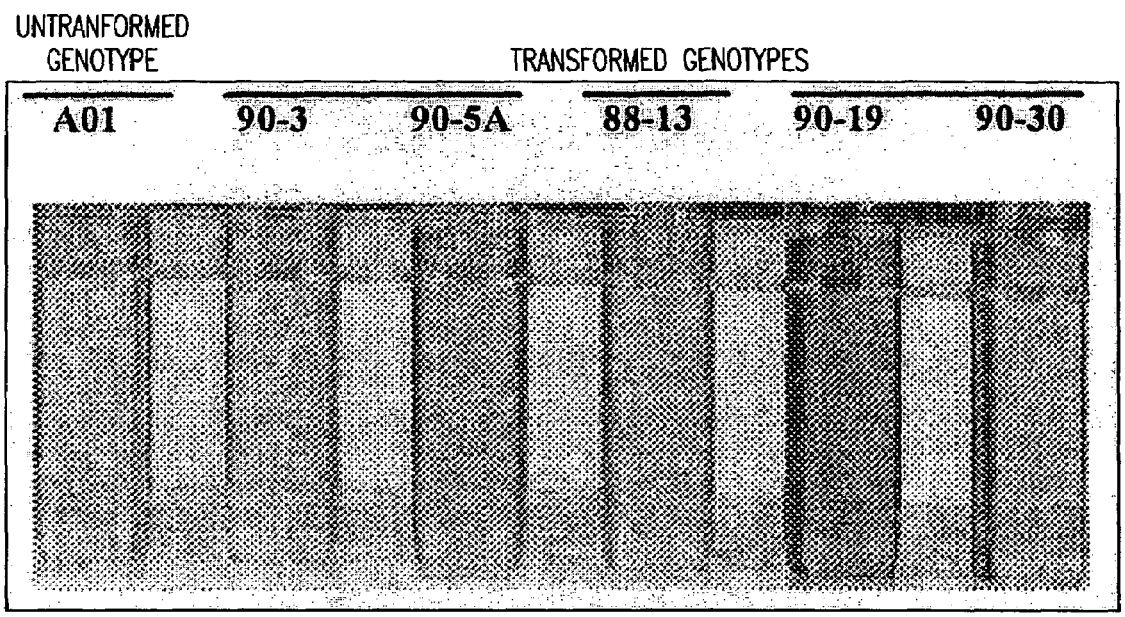
Figure 2E:
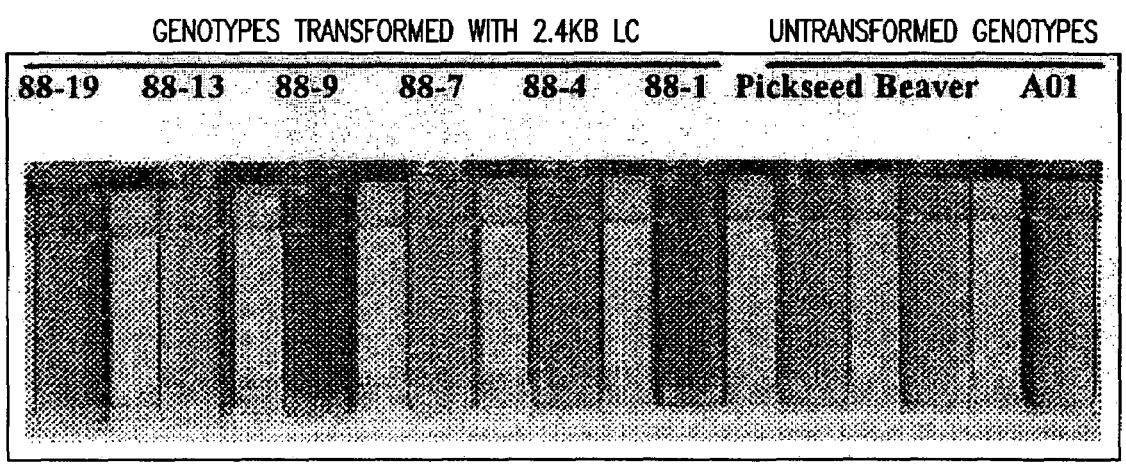
Figure 2F:
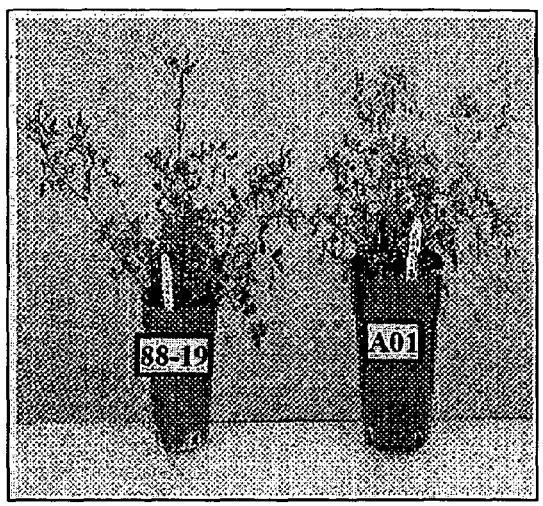
Figure 2G:
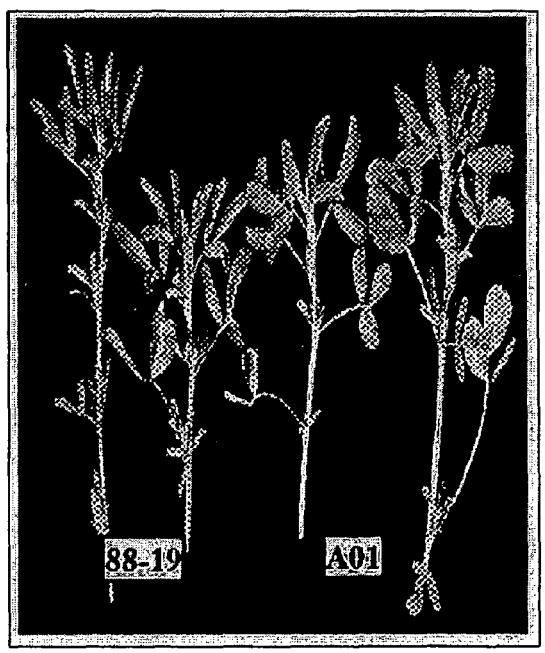
Figure 2H:
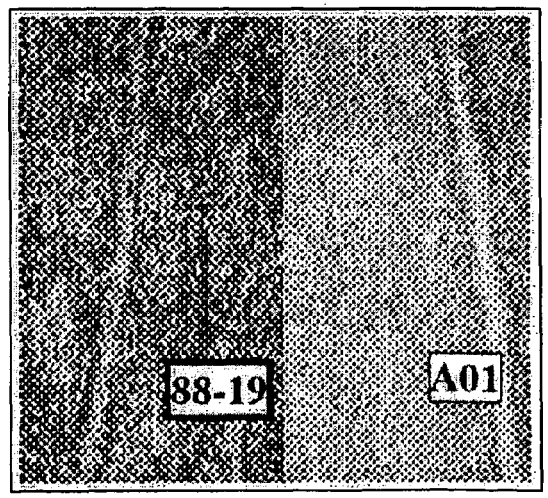

In initial experiments using the 2.2 kb Lc transgene, a red phenotype was observed in small Lc-transgenic plants (Family 90) as they were adjusting to growth in the greenhouse after tissue culture (FIG. 1C). This red phenotype became less distinct and finally was completely obscured as plant forage assumed the normal green colour of the untransformed parent genotype during subsequent growth under normal greenhouse conditions (20° C., <600 uE). Northern blots of RNA from the Lc-transgenic alfalfa plants growing in the greenhouse showed expression of Lc in several of the transgenic plants in addition to enhanced expression of CHS, the first structural enzyme of the flavonoid pathway (FIGS. 1D-F). This gene expression pattern was evident under growth conditions which did not induce a conspicuous accumulation of anthocyanins, indicating that Lc likely stimulates expression of CHS constitutively in the transgenic alfalfa.

After Family 88 of transgenic plants also had been established, selected genotypes of the two families were cloned as rooted cuttings. A larger proportion of Lc-expressing genotypes from Family 88 developed a red leaf phenotype during this rooting in the greenhouse compared with Family 90 genotypes (Table 2). Once rooted, plants were repotted into 3.5' pots and allowed to grow in the grouse, during which time the red phenotype was again repressed. Subsequently, plants were exposed to controlled stress conditions similar to those that field plants would normally endure eg. cold temperature (FIG. 2, Panels B and C; Table 3) or natural wind and daylight (FIG. 2, Panels D-H). At the end of each exposure period, gene expression was characterized and anthocyanin extracted.

After a period of exposure to cold and low light intensity, a red phenotype was observed in transgenic plants which expressed the Lc gene. When examined in detail, anthocyanins accumulated and banding patterns for Lc RNA were altered in both leaf and stem in both families of plants in genotypes which expressed Lc (FIG. 2, Panel B and C). With Family 90 transgenics, steady state levels of CHS and F3H RNA patterns in stems appear stronger in the cold in the red phenotypes, while expression patterns for these structural genes did not appear to change with the presence of Lc (FIG. 2 Panel C). Gene expression for Lc and F3H was induced in the cold relative to normal greenhouse conditions in leaves of genotype 88-19 (FIG. 2, Panel B; Table 3). Upon return to normal greenhouse conditions, the red phenotype was lost in these plants. B-Peru-transgenic plants did not develop a red phenotype even after 13 days of cold conditioning.

Potted transgenic genotypes were also placed outside during daytime in the Saskatoon Research Centre farmyard to determine the effect of natural light. A larger number of genotypes in Family 88 tended to develop a darker red phenotype with extractable anthocyanins under these conditions compared with Family 90 (FIG. 2, Panels D and E). In addition, most plants in Family 88 developed the coloured phenotype noticeably within one day compared with Family 90 (Table 2). When examined in more detail in genotype 88-19, anthocyanins were accumulated in leaf mesophyll cells (FIG. 2, Panels F-H). The changes to the Lc-transgenic alfalfa under cold and natural light occurred in spite of the fact that the Lc transgene is under the control of the "constitutive" CaMV35S promoter.

Selected genotypes of the two Lc-trasgenic families were also transplanted into a field trial at the Saskatoon Research Centre farm in early July. Plants containing the Lc transgene established and grew as well as control parent plants and B-Peru-transgenic plants. The red phenotype in Lc-transgenic field plants directly mirrored the response of each genotype in the natural light experiment throughout the field season. All plants grew well in the trial, despite unusually dry and windy conditions. However, B-Peru transgenic plants never developed a red phenotype during the field trial.

Field-grown forage without floral shoots was harvested at the end of September for analysis. The colour phenotype and relative anthocyanin content in these transgenic plants correlated with Lc and CHS RNA levels (FIG. 3, Table 4). However, F3H and DFR transcripts were not detected in this material and are likely induced transiently during changes in growth conditions rather than in adapted plants. Genotypes from Family 88 tended to produce relatively greater quantities of anthocyanin in the field material compared with those from Family 90. These data together with the data in Table 2 indicate that the 2.4 kb Lc may interact more efficiently with the alfalfa leaf gene regulation machinery to enhance concentrations of flavonoid metabolites that are required to produce lower pathway endproducts compared with either the 2.2 kb Lc gene or B-Peru. They indicate that the 200 bp untranslated region on the Lc (2.4 kb) gene acts as an enhancer in some fashion in alfalfa rather than the repressor function which occurs in maize and Arabidopsis (Lloyd et al., 1992). Reversion of the red phenotype upon relief from any of the stress conditions established (cold, high light intensity, transplantation) supports a mechanism in which Lc may be stabilized by an alfalfa stress-induced protein. A detailed examination of phenolics by HPLC and HPLC-MS in three of the Lc-transgenics indicated that Lc has re-directed flavonoid biosynthesis to produce the anthocyanins by reducing the overall content of flavones normally present in the non-transformed parent genotype (Table 5). This appears to be at the expense of luteolin flavone, since the relative proportion of luteolin and apigenin is altered (Table 6). At least 4 different anthocyanin species are induced in the transgenic plants, as indicated by TLC.

By plant transformation is meant the introduction of an external nucleic acid sequence into the plant genome. Transformation techniques include calcium phosphate transfection, DEAE-Betran transfection, elecroporation, microinjection, protoplast fusion and liposome-mediated transfection. Alternatively, a plant virus such as CaMV may be used as a vector for introducing foreign nucleic acid into plant cells or a high velocity ballistic penetration using small particles (Klein et al., 1987). A most preferred method for introducing nucleic acid segments into plant cells is to infect a plant cell or plant tissue with *Agrobacteriun tumefaciens* which has been transformed with a selected nucleic acid segment (Horsch et al., 1984). Alfalfa was transformed following the protocol of McKersie et al., 1996. Other methods of alfalfa transformation either via, *Agrobacterium* or using other biological, chemical or physical methods are feasible and thus may be used in the present invention. Methods for producing appropriate vectors, for transforming cells with those vectors and for identifying transformants are described in the scientific literature, as for example, but not limited to, Sambrook et al. (1989), *Molecular Cloning: A Laboratory Manual*, Cold Spring Harbor Laboratory Press, Cold Spring Harbor, N.Y., Gelvin and Schilperoort (1991) *Plant Molecular Biology Manual*, Kluwer Academic Press, and more importantly in Glick, B. R. and Thompson, J. E. 1993, *Methods in Plant Molecular Biology and Biotechnology*, CRC Press, Boca Raton.

The cellular distribution of the Lc gene product in tissues may be analyzed by quantitative reverse transcriptase PCR analysis or by Northern blot analysis. Antibodies to the gene product can also be generated for several applications including both immunuocytochemical and immunofluorescence techniques to visualize the proteins directly in cells and tissues in order to establish the cellular location of the protein.

Methods for analyzing anthocyanins, condensed tannins and flavonoids are described in the scientific literature, as for example but not limited to Harborne (1998), Maybry et al., 1970 and Skadhauge et al., 1997).

The present invention provides transgenic alfalfa that are stably and consistently transformed with an Lc nucleic acid sequence resulting in altered anthocyanin and condensed tannin levels in these plants. As such, these transformed plants have several uses in a variety of applications.

Use of Lc to Alter Alfalfa Tannin Levels for the Improvement of Forage Quality

The Lc gene sequences or closely related genes may be used to transform legume forage plants to increase their quality by increasing tannin levels, for example in alfalfa (lucerne, *Medicago sativa* and *M. falcata*) or in other such highly-nutritious protein-rich forage/feed for ruminants, such as sweetclover, red clover, white clover, alsike clover, or subterranean clover, providing strong economic benefits to the beef, dairy, and sheep industries. First tannins eliminate the close-celled, protein-stabilized foam, which forms in the rumen and causes bloat (Howarth et al., 1991; Lees, 1992; Tanner et al., 1995; Coulman, 1999). This foam presses outward and may press so strongly on the diaphragm that the animal suffocates and dies. In milder forms, bloat causes cattle to go off their feed and gain weight more slowly. Bloat is the major constraint to raising and maintaining cattle and sheep on pasture with more than 50% alfalfa or white clover.

Second, an excessive initial rate of digestion occurs in the rumen with soft-leafed legumes such as alfalfa and white clover, resulting in a significant loss of protein to urea and ammonia (15-25% for alfalfa). Condensed tannins "capture" this protein (called protein bypass or ruminal escape protein) by lowering the initial rate of digestion and improving peptide and amino acid flow to the small intestine (Tanner et al., 1994; Waghorn et al., 1997; McNabb et al., 1993). Hence, tannins in forage legumes should significantly improve the efficiency of conversion of alfalfa and white clover protein to ruminant meat protein, milk and wool (Min et al., 1998). Third, condensed tannins will reduce the activity of bacteria and fungi which can spoil high protein legume silage such as alfalfa and white clover. Fourth, the capture of a greater proportion of alfalfa and white clover protein into meat, milk and wool may result in reduced ammonia smell and methane/$CO_2$ production (greenhouse gas pollution) arising from high-intensity beef and dairy operations (Waghorn, 1997). Fifth, condensed tannins in forage and feed may improve overall ruminant health. For example, cattle and sheep feeding on mixtures which include tannins show a reduced parasite load in their intestines compared with mixtures without tannin (Neizen et al., 1995; Waghorn et al., 1997).

Studies at the Brandon Research Station (Agriculture and Agri-Food Canada) indicate that approximately 60% of beef steers and 100% of heifers can be finished off inexpensively if grazed directly on 100% alfalfa pasture, compared with the usual but costly 90-day grain-fed stay in a feedlot, as long as the herd was carefully managed to prevent bloat. The remainder could be finished with about 30-60 feedlot days. Dramatically lowered costs can be obtained even when cattle are raised in mixed pastures which include alfalfa. For example, a month of grazing on a 50% sainfoin-50% alfalfa irrigated pasture (where sainfoin forage contains 3-8% fresh weight in condensed tannins) yielded weight gains in cattle comparable to those achieved in a feedlot, and without any bloat.

Improvements to alfalfa forage quality using condensed tannins can be made without compromising high nutritional index and total digestability, particularly for alfalfa. Forage legumes such as sainfoin (*Onobrychis viciifolia*) and birdsfoot trefoil (*Lotus corniculatus*) do not cause bloat in ruminants. This has been connected to the presence of condensed tannins in their leaves. These plant species display a total nutritional digestibility and in vitro gas production which is similar to that produced by alfalfa at comparable growth stages (Fay et al., 1980). The variation in response by ruminant microorganisms and intestinal parasites when exposed to condensed tannin may be at the root of the improvement noted when tannin-containing plant species are fed to ruminants (Bae et al., 1993a; 1993b; Jones et al., 1994). Other methods of bloat control by cultivating mixed species pastures and by adding purified tannin as a prophylactic into the drinking water are projected to be less cost-effective or more management-intensive than a tannin-containing variety of alfalfa. In accordance with a further aspect of the invention, one can also reduce the tannin content of alfalfa and other legumes, for example by suppressing expression of the Lc genes or related native genes. Some plant species have such high leaf condensed tannin content that they become unpalatable to livestock and some wildlife. Examples include browse species in the tropics (Mangan, 1988; Furstenburg, 1994) and cicer milkvetch (*Astragalus cicer*). The invention permits the manipulation of the tannin content of such species.

Use of Lc in Alfalfa for Producing Optimal Condensed Tannin Levels for Ruminant Forage The development of high quality forage depends not only on the induction of genes to enable tannin biochemistry to function, but also on the optimization of tannin content in relation to the plant source. The Lc regulatory gene can be used to transform alfalfa to regulate the content of condensed tannin, opening the possibility to tailor tannin content for alfalfa and other forage species. One research group recently estimated that 0.5% dry matter tannin would give complete bloat-safety (Li et al., 1996). Another group predicted a 10-15% increase in meat, milk and wool production, if 2-3% dry matter tannin was present in the animal diet (McNabb et al., 1993). Studies indicate that major rumen fibre-digesting and protein-digesting bacteria and fungi can tolerate as much as 200 µg/ml of tannin with no loss of viability and with no change in normal digestion rates (Bae et al., 1993a,b; Jones et al., 1994). This dose is well within the range for bloat-safety. Higher doses of tannin did cause problems in digestion in these latter studies, the maximum acceptable tannin dose varied with the plant source. In these latter studies, purified sainfoin tannins caused the fewest difficulties to rumen bacterial digestion profiles. However, the source of the tannins proved unimportant for ruminal foam reduction in vitro (Tanner et al., 1995).

Use of Lc to Reduce Tannin Levels to Reduce Protein Haze in Beer and Juice

Barley contains condensed tannin in the testa layer of the seed coat. The condensed tannins are released during processing of malting barley and cause a haze of precipitated protein to form slowly in beer during cold storage. Considered undesirable to the appearance of beer, these precipitates are removed by chemical filtration before bottling. Haze-free cultivars of barley lacking testa condensed tannin have been developed by chemical mutagenesis programs (Erdal, 1986; von Wettstein et al., 1979; Outtrup, 1992), but the resultant plants required considerable backcrossing and intercrossing to develop high yielding malting barley lines. The ability to reduce condensed tannin in malting barley, for example by transformation with an antisense Lc gene, therefore has application for breeders in the brewing industry.

Use of Lc to Alter Plant Tannin Levels as Deterrents to Insects, Fungi, Bacteria and Birds Condensed tannins are thought to be a broad spectrum defence strategy against herbivores and pathogens for many plant species. As a result, the novel Lc genes of the present invention can be used to transform alfalfa and other selected legumes in order to increase condensed tannin levels and as a result provide resistance or deterrence against pathogens, insects and birds.

When tested for their effect on insect pests, condensed tannin efficacy is dependent on concentration and whether the insect is able to tolerate or deactivate the condensed tannin. Insects not normally subjected to tannin diets or specialist insects are especially vulnerable. For example, condensed tannins inhibited growth of grasshoppers at high doses, but did not deter their feeding; while the crucifer flea beetle (*Phyllotreta crucifera*) and diamondback moth (*Plutella* spp.) were inhibited from feeding at lower doses (Muir et al., 1999). Other insect pests are known to be affected by condensed tannins as well.

Condensed tannins also have antifungal and antiviral properties. Scab-resistant apples have higher amounts of flavan-3-ols in leaf and fruit skins (Treutter and Feucht, 1990), and grain mould is inhubited by tannins (Jambunathan et al., 1986). The potency of condensed tannins as an antifungal agent can be dependent on the specific structure of the polymer. For example, the potency of the cocao procyanidin against *Crimpellis perniciosa* correlated with increasing polymer molecular weight (Brownlee et al., 1992). Other fungal pathogens known to be inhibited by condensed tannins include Fusarium (Skadhauge, 1996; Skadhauge et al., 1997; von Wettstein and Hagie, 1998). Plant viruses can also be inhibited with condensed tannins (Zhang et al., 1990).

Birds can also be deterred from feeding on crops by condensed tannins. Bird-deterring sorghum lines are rich in condensed tannins compared with lines which are susceptible (Reed et al., 1987).

Use of Lc to Alter Tannin Levels in Seeds and Grains to Improve Seed Quality in Oilseeds and Grain Legumes Reduction of tannins in specific tissues of oilseed and grain legume species would improve their feed and food quality and industrial potential. For crops such as rapeseed (canola) and soybean, which are fractionated chiefly into oil and a protein component used for animal feed, seed coat tannins contribute to the indigestible fibre fraction and are detrimental to the total value of the crop (Simbaya et al., 1995). Health and digestion of poultry and swine can be negatively affected by even low quantities of dietary condensed tannins in their diets. Tannins in rapeseed feed are considered the basis for the fishy smell in tainted eggs, since tannins block metabolism of trimethylamine to an odorless compound by inhibiting TMA oxidase (Naczk and Shahidi, 1992). Mutant barley lines that are free of condensed tannins in the seeds have been developed and, when used in feed, give improved rates of weight gain in chickens (Jende-Strid, 1993; Newman et al., 1984).

For grain legume crops such as lentils (*Lens culinaris*), peas (*Pisum sativum*) and soybeans (*Glycine max*), varieties with low or no condensed tannin in the seed coat are preferred particularly for human consumption because of the bitterness of these compounds; tannin-free varieties may command a premium price. Reduction of seed coat condensed tannin in canola meal might also increase the potential of canola meal for the human food market.

While mutants and variants with low or no levels of seed coat tannin exist in several of these species, use of an antisense Lc regulatory gene introduced by transformation allows the quick adaptation of good varieties to these higher-value uses.

Use of Lc for Nutraceutical Applications

Condensed tannins have been shown to inhibit a variety of enzymes such as xanthine oxidase (Costantino et al, 1992) and protein kinases (Polya and Foo, 1994). Plant extracts containing condensed tannins have been used to inhibit pectinase and cellulase (Bell et al., 1962). Condensed tannins are excellent antioxidants. The measured efficiency compared with known antioxidants such as vitamin E and B-hydroxytoluene or B-hydroxyanisol is dependent on the plant source, the polymer structure, and the method of measurement (Muir, 1997). Crude extracts containing high concentrations of condensed tannins from red and black currents, red and black raspberries and highbush blueberries are all highly active at scavenging superoxide radicals (Costantino et al., 1992). The UV absorptive properties of condensed tannins lend additional potential for plants containing condensed tannins to be used in skin creams and sunprotectants. This information suggests that plants developed with a transgene which stimulated condensed tannin biosynthesis such as the Lc gene of the present invention may have potential as health foods and nutraceuticals.

Use of Lc to Affect Flavour Colour and Taste of Food and Wine

Condensed tannins contribute to the astringency, bitter flavours, and colour in fruit, fruit juice and red wine (Lea, 1982; Singleton, 1992). These characteristics are in proportion to their content and polymer size. For example in cider, a maximum perceived bitterness response occurred with tetrameric procyanidin, while the response for astransgency continued to increase with molecular size (Lea, 1992). Since they are easily oxidizable phenolics, condensed tannins contribute to the browning that occurs when fruit spoils. Their presence coupled with chlorogenic acid makes a major contribution to the light yellow/brown colour of apple juice (Lea. 1992). In red wine, anthocyanins covalently link with condensed tannins, preventing them from precipitating with proteins (Singleton, 1992). The tannins contribute to the warmer colour tones of matured red wine (Liao et al., 1992). A gene such as Lc which would regulate tannin content may have use in the control of these characterstics.

In summary, the present invention provides transgenic alfalfa plants containing an expressible Lc nucleotide sequence that have improved characteristics for use, such as improved forage quality. The expression of the inserted Lc sequence alters the biosynthesis and accumulation of flavonoid compounds including anthocyanin and condensed tannin. The present invention also encompasses methods of making such transgenic plants as well as uses of such plants in various applications.

EXAMPLES

The examples are described for the purposes of illustration and are not intended to limit the scope of the invention.

Methods of synthetic chemistry, protein and peptide biochemistry and molecular biology referred to but not explicitly described in this disclosure and examples are reported in the scientific literature and are well known to those skilled in the art.

Transformation of Alfalfa

Alfalfa was transformed with the maize Lc anthocyanin regulatory gene in order to stimulate production of the flavonoid pathway. Two different gene constructs were used, one encoding a 2.2 kb Lc gene and the second encoding a 2.4 kb Lc gene containing a 200 bp 5'-untranslated region as outlined in Lloyd et al. (1992). Both constructs were subcloned in a similar way and expressed by a single CaMV35S promoter. In addition, alfalfa was transformed with a homologue from maize, B-Peru (Chandler et al., 1989) under the control of an enhanced CaMV35S promoter in order to determine the specificity of the gene sequence required to function in alfalfa. Alfalfa transformation was done using a standard Agrobacterium method (McKersie et al., 1996). Kanamycin was used to select transformed material which was then transferred to shoot induction medium. When shoots had formed, they were rooted and initially placed in pots containing fine pebbles and fed hydroponically in the greenhouse. Plants were later grown in a potting soil. Plants transformed with the Lc construct were observed to have strong red colour throughout leaves and stems, indicative of anthocyanin accumulation (FIG. 1C). Anthocyanin occsionally accumulates in alfalfa if it is diseased or senescent, but anthocyanin is not normally observed in young, fast-growing alfalfa such as these transgenic plants. Typical of plant transformation, a range of phenotype expression was observed.

Identification and Molecular Analysis of Transgenic Plants by PCR, Southern and Northern Blots Unless otherwise detailed, molecular biology procedures were carried out following standard methods such as those described in Sambrook et al., 1989; Ausubel et al., 1999; Gelvin et al., 1998 and Griffin and Griffin, 1994. Transgenic plants expressing the nptII gene were identified by PCR; those positive by PCR were then characterized for the presence of the Lc transgene using Southern blotting methods on digested DNA (FIGS. 1A, 1B) All plants accumulating anthocyanin were among the plants which Southern blots also identified as containing Lc. Northern blots probed with the Lc gene and CHS gene were carried out on plants growing in the greenhouse after much of the initial red phenotype had faded in order to select genotypes for induction experiments and the field trial. Although Lc expression at this period of plant selection was minimal, stimulation of CHS expression over the level of control plants was still observed (FIG. 1F).

Gene expression studies were conducted under a variety of growth conditions using potted clones of each transgenic genotype and untransformed genotype developed from rooted cuttings. Clones were cut back to 3" height, allowing some leafy material to remain, and exposed to 4° C. in a confined growth cabinet for 10 days (Lc-plants) or 13 days (B-Peru-plants). Larger plants were also exposed to natural daylight and wind conditions outside in a farmyard for 9 h per day for periods of 5 days during May and June, 2001, and then returned into a greenhouse at night. Young flower buds were continuously removed on outside plants before they matured and opened. At the end of these periods, plants were photographed and leaves and stems were harvested, frozen in liquid $N_2$ and stored for RNA and anthocyanin traction, and plants were returned to normal greenhouse conditions. RNA was also extracted from field-grown material. RNA was tested for the expression of Lc, CHS, F3H and DFR. Plant clones were also grown for 1-2 week periods in two different greenhouses and growth cabinets to determine the minimum light conditions required for phenotype selection.

Plant genomic DNA was prepared by a modified Dellaporta method or using a Quiagen plant DNA mini-columns. For Southern blot analysis, 10 ug DNA was digested overnight with 50 U HindIII, separated on agarose gels, denatured using 0.4 M NaOH, and blotted overnight onto nylon membranes (Doehninger-Mannheim). RNA for Northern blot analysis was prepared by using a RNA preparatory column (Quiagen) for untransformed alfalfa tissues or by the borax method for high phenolic plant tissues, since phenolics interfere with RNA isolation by most methods (Wilkins and Smart, 1996). $^{32}$P-labelled DNA probes were prepared from gel-purified digested plasmid DNA fragments using a standard random priming kit (GilbcoBRL) including: Xba I digestion of pKYXL71 to recover the complete Lc gene Lloyd et al, 1992); EcoRI digestion or PCR amplification to recover either the whole or a 500 bp fragment of the alfalfa CHS cDNA (Genrank, Junghans et al., 1993), and PCR amplification to recover the alfalfa F3H and DFR genes (Genbank, Charrier et al., 1995). Radiolabelled probe fragments were purified from unincorporated nucleotides using a S-300 column (Pharmacia). Northern and Southern hybridization was conducted using standard methods, followed by washing the blots to moderate or high stringency.

Development of Field Trial:

A subset of Lc-transgenic alfalfa genotypes were cloned by rooted cuttings, grown in root trainer containers, then transplanted to a 16 m×24 m spaced-plant field plot located at the Saskatoon Research Centre farm in early July, 2001. Six plants of each genotype (4 reps) were established in 1 m rows, 3 plants per m within each row. Plants were lightly watered 3 times during the initial phase to establish growth, otherwise were allowed to grow under extremely dry, windy, and natural light summer conditions until late September. Growth and phenotype were observed weekly. The field trial was monitored twice weekly for flower bud development and damage from insects and other foragers such as rabbits. Young flower buds were continuously removed on before they matured and opened. Weeds were removed by hand and rabbits deterred by a wire-mesh fence. Forage was harvested manually on Aug. 20, 2001 and Sep. 29, 2001, frozen immediately in liquid $N_2$ in plastic bags, and stored on dry ice or in a −80° C. freezer until proessed. Frozen forage from September. 20th was used to extract RNA, anthocyanins and flavonoids.

Extraction and Quantitation of Anthocyanin and Flavonoids

Standard methods such as those from Mabry et al. (1970) and Harborne (1998) were used to determine anthocyanins and flavonoids. Anthocyanins were extracted from frozen leaf material of a range of transgenics and the parent A01 genotype by acid hydrolysis (10 vol 2M HCL, 55° C., 10 min), followed by overnight extraction at 22° C. Samples were centrifuged and anthocyanin quantified by measuring $A_{525}$ of the cleared supernatant using a scanning spectrophotometer. Leaf material was also hydrolyzed for 45 min at 80° C. from genotype 88-19 and A01 and the cleared supernatant extracted 3 times with ethyl acetate to remove flavonoid aglycones. The aqueous phase containing anthocyanins was chromatographed using equivalent loading on thin layer plates (butanol:acetic acid:water 4:1:5 v/v/v in the $1^{st}$ dimension and 15% acetic acid in the $2^{nd}$ dimension) and observed under visible and UV light Frozen leaf and stem from A01 and transgenic genotypes 88-4, 88-19 and 90-19 were hydrolyzed in 2M HLC for 30 min, then fractionated on a Waters Oasis C18 Sep Pak cartridge using a methanol step gradient. The MeOH fractions were then separated on a Symmetry RF-C18 columm using a Waters 2690 "Alliance" HPLC equiped with a photo-diode-array detector, Millenium software, and a water-acetonitrile gradient solvent system modified with 0.05% trifluoroacetic acid. Samples were also analyzed using an Alliance RP HPLC system with a benchtop mass spectrometer (Quattro LCZ) (MicroMass Co.).

It is known that modifications and variations of the present invention as set forth herein may be made without departing from the spirit and scope thereof or the scope of the appended claims. The specific embodirneirts described herein are given by way of example only and the invention is not limited thereto.

BIBLIOGRAPHY

Babwah, A., Brown, G. G. and Waddell, C. S. 1998. Development of selectable and screenable markers in *Brassica napus*. $11^{th}$ Int.'l Crucifer Genetics Workshop. Quebec, Canada. P-31.

Bae, H.-D., McAllister, T. A., Muir, A. D., Yanke, L. J., Bassendowski, K. A. and Cheng. K.-J. 1993a J. Agric. Food Chem. 41: 1256-1260.

Bae, H.-D., McAllister, T. A., Yanke, J., Cheng, K.-J. and Muir, A. D. 1993b Appl. Environ. Micro. 59: 2132-2138.

Bell, T. A., Etchells, J. L., Williams, C. F. and Porter, W. L. 1962. Inhibition of pectinase and cellulase by certain plants. Bot. Gaz. 123: 220-223.

Beveridge, T., Harrison, J. E. and Weintraub, S. E. 1997. Procyanidin contributions to haze formation in anaerobically produced apple juice. Food Science and Technology 30: 594-601.

Bradley, J. M.; Davies, K. M.; Deroles, S. C.; Bloor, S. J.; Lewis, D. H. The maize Lc regulatory gene up-regulates the flavonoid biosynthetic pathway of petunia Plant J. 13:381 (1998).

Bradley, J. M., Deroles, S. C., Boase, M. R., Bloor, S., Swinny, E. and Davies, K. M. (1999) Variation in the ability of the maize Lc regulatory gene to upregulate flavonoid biosynthesis in heterologous systems. Plant Sci. 140: 31-39.

Brownlee, H. E., Hedger, J. and Scott, I. M. 1992. Effects of a range of procyanidins on the cocoa pathogen *Crinipellis perniciosa*. Physiol. Mol. Plant Pathol. 40: 227-232.

Butler, L. G. Relative degree of polymerization of sorghum tannin during seed development and maturation. *J. Agric. Food Chem*. 30:090 (1982).

Chandler, V. L., Radicella, J. P., Robbins, T. P., Chen, J., Turks, D. Two regulatory genes of the maize anthocyanin pathway are homologous: Isolation of the B utilizing R genomic sequences. Plant Cell 1: 1175 (1989).

Charrier, B.; Coronado, C.; Kondorosi, A.; Ratet, P. Molecular characterization and expression of alfalfa (*Medicago sativa* L.) flavanone-3-hydroxylase and dihydroflavonol-4-reductase encoding genes. *Plant Mol. Biol.* 29:773 (1995).

Cone, K. C.; Burr, F. A.; Burr, B. Molecular analysis of the maize anthocyanin regulatory locus C1. *Proc. Nat'l. Acad. Sci.* (*USA*) 83:9631 (1986).

Constantino, L., Albasini, A, Rastelli, G. and Benvenuti, S. 1992. Activity of polyphenolic crude extracts as scavengers of superoxide radicals and inhibitors of xanthine oxidase. Planta Med. 58: 342-344.

Damiani F.; Paolocci, F.; Consonni, G.; Crea, F.; Tonelli, C.; Arcioni, S. A maize anthocyanin transactivator induces pigmentation in hairy roots of dicotyledenous species. *Plant Cell Rep*. 17:339 (1998).

Damiani F.; Paolocci, F.; Cluster, P. D.; Arcioni, S.; Tanner, G. J.; Joseph, R. G.; Li, Y. G.; deMajnik, J.; Larkin, P. J. The maize transcription factor Sn alters proanthocyanidin synthesis in transgenic *Lotus corniculatus* plants. *Aust. J. Plant Phys*. 26:159-169.

de Majnik, J.; Tanner, G. J.; Joseph, R. G.; Larkin, P. J.; Weinman, J. J.; Djordjevic, M. A.; Rolfe, B. G. Transient expression of maize anthoevanin regulatory genes influences anthocyanin production in white clover and peas. *Aust. J. Plant Physiol*. 25:335 (1998).

Erdal, K. Proanthocyanidin-free barley. *J. Inst. Brewing* 92:220 (1986).

Fay, J. P., Cheng, K. J., Hanna, M. R., Howarth, R. E. and Costerton, J. W. 1980. In vitro digestion of bloat-safe and bloat-causing legumes by rumen microorganisms: Gas and foam production. J. Dairy Sci. 63: 1273-1281.

Furstenburg, D.; van Hoven, W. Condensed tannin as antidefoliate agent against browsing by giraffe (*Giraffa camelopardalis*) in the Kruger National Park. Comp. Biochem. Physiol. 107A:425 (1994).

Gelvin, S. B. and Schilperoort, R. A. 1991. Plant Molecular Biology Manual. Kluwer Academic Publ. Boston.

Glick, B. R. and Thompson, J. E. 1993. Methods in Plant Molecular Biology and Biotechnology. CRC Press. Boca Raton.

Goodrich, J.; Carpenter, R.; Coen, E. S. A common gene regulates pigmentation pattern in diverse plant species. *Cell* 68:955 (1992).

Goplen, B. P.; Howarth, R. E.; Sarkar, S. K.; Lesins. K. A. search for condensed tannins in annual and perennial species of *Medicago, Trigonella*, and *Onobrychis. Crop Sci*. 20:801(1980).

Gruber, M. Y., Ray, H., Auser, P., Skadhauge, B., Falk J., Thomsen, K. K., Stougaard, J., Muir, A., Lees, G., Coulman, B., McKessie, B., Bowley, S. and von Wettstein, D. 1999. Genetic systems for condensed tannin biotechnology. In: Gross, G. G., Hemingway, R. and Yoshida, T. (Eds.) Plant polyphenols 2: Chemistry, Biology, Pharmacology, Ecology. Plenum Press, New York. pp 315-341.

Gruber, M. Y., Skadhauge, B. and Stougaard, J. 1996. Condensed tannin mutations in *Lotus japonicus*. Polyphenol Letters. 18: 4-8.

Hagerman, A. E. and Butler, L. G. 1981. The specificity of proanthocyanidin-protein interactions. J. Biol. Chem. 256: 4494-4497.

Harborne, J. B. 1998. Photochemical Methods: a guide to modern techniques of plant analysis. Chapman and Hall, Inc., London.

Harborne, J. B. and Williams, C. A. 1995. Anthocyanins and other flavonoids. Natural Product Reports. 12: 639-657

Horsch, R., Fraley, R., Rogers, S., Sanders, P., Lloyd, A. and Hoffman, N. 1984. Inheritance of functional foreign genes in plants. Science 223: 496-498.

Howarth, R. E.; Chaplin, R. K.; Cheng, K.-J.; Goplen, B. P.; Hall, J. W.; Hironaka, R.; Majak, W.; Radostits, O. M. Bloat in cattle. Agriculture Canada Publication 1858/E. Communications Branch Agriculture and Agri-Food Canada, Ottawa (1991).

Jambunatlan, R., Butler, L. G., Bandyopadhyay, R. and Mughogho, L. K. 1986. Polyphenol concentrations in grain, leaf, and callus tissues of mold-susceptible and mold-resistant sorghum cultivars. J. Agric. Food Chem. 34: 425-429.

Jende-Strid, B. Genetic control of flavonoid biosynthesis in barley. *Hereditas* 119:187 (1993).

Koorneef, M. Mutations affecting the testa colour in *Arabidopsis. Arabid. Inf. Service* 27:1 (1990).

Jones, G. A.; McAllister, T. A.; Muir, A. D.; Cheng, K.-D. Effects of sainfoin (*Onobrychis viciifolia* Scop.) condensed tannins on growth and proteolysis by four stains of ruminal bacteria *Appl. Environ. Microbiol*. 60:1374 (1994).

Joseph, R.; Tanner, G.; Larkin, P. Proanthocyanidin synthesis in the forage legume *Onobrychis viciifolia*. A study of chalcone synthase, dihydroflavonol 4-reductase and leucoanthocyanidin 4-reductase in developing leaves. *Aust. J. Plant Physiol*. 25:27 (1998).

Junghans, H.; Dalkin, K.; Dixon, R. A. Stress responses in alfalfa (*Medicago sativa* L.). Part 15. Characterization and expression patterns of members of a subset of the chalcone synthase multigene family. *Plant Mol. Biol*. 22:239 (1993).

Klein, T. M., Wolf, E. D., Wu, R. and Sanford, J. C. 1987. High-velocity microprojectiles for delivering nucleic acids into living cells. Nature 327: 70-73.

Koorneef, M. 1991. The complex syndrome of ttg mutants. Arabidopsis Information Service 18: 45-51.

Kornneef, M., Dellaert, L. W. M. and van der Veen, J. H. 1982. EMS- and radiation-induced mutation frequencies at individual loci in *Arabidopsis thaliana* (L.) Heynh. *Mutation Research* 93: 109-123.

Koupai-Abyazani, M. R.; McCallum, J.; Muir, A. D.; Bohm, B. A.; Towers, G. H. N.; Gruber, M. Y. Developmental changes in the composition of proanthocyanidins from leaves of sainfoin (*Onobrychis viciifolia* Scop.) as determine by HPLC analysis. *J. Agr. Food Chem.* 41:1066 (1993a).

Koupai-Abyazani, M. R.; McCallum, J.; Muir, A. D.; Lees, G. L.; Bohm, B. A.; Towers, G. H. N.; Gruber, M. Y. Purification and characterization of a proanthocyanidin polymer from seed of alfalfa (*Medicago sativa* cv. Beaver). *J. Agric. Food Chem.* 41:565 (1993b).

Larkin, P. J.; Yuguang, L.; Tanner, G. J.; Banks, P. M. Using alien genes—translocations, transfusions and transgressions. In: Focused Plant Improvement. Towards Responsible and Sustainable Agriculture. *Proc. Tenth Australian Plant Breeding Conference*. Gold Coast, Australia (April) (1993).

Lea, A. G. H. 1992. Flavor, color, and stability in fruit products: The effect of polyphenols. In: Hemingway, R. W.; Laks, P. E. (eds.) Plant Polyphenols: Synthesis, Properties, Significance. Basic Life Sciences vol. 59. Plenum Press, New York. pp. 827-848.

Lees, G. L. Condensed tannins in some forage legumes: their role in the prevention of ruminant pasture bloat. 1992. In: Hemingway, R. W.; Laks, P. E. (eds.) Plant Polyphenois: Synthesis, Properties, Significance. Plenum Press, New York. pp 914-934.

Lees, G. L., Wall, K. M., Beveridge, T. H. and Suttill, N. H. 1995. Localization of condensed tannins in apple fruit peel, pulp, and seeds. Can. J. Bot. 73: 1897-1904.

Li, Y. G., Tanner, G. and Larkin, P. 1996. J. Sci. Food Agric. The DMACA-HCl protocol and the threshold proanthocyanidin content for bloat safety in forage legumes. 70: 89-101.

Liao, H., Cai, Y. and Haslam, E. 1992. Polyphenol Interactions. Anthocyanins: Co-pigmentation and colour changes in red wines. J. Sci. Food Agric. 59: 299-305. Beveridge, T., Harrison, J. E. and Weintraub, S. E. 1997. Procyanidin contributions to haze formation in anaerobically produced apple juice. Food Science and Technology 30: 594-601.

Lloyd, A. M.; Walbot, V.; Davis, R. W. *Arabidopsis* and *Nicotiana* anthocyanin production activated by maize regulators R and C1. Science 258:1773 (1992).

Ludwig, S. R; Habera, L. F.; Dellaporta, S. L.; Wessler, S. R. Lc, a member of the maize R gene family responsible for tissue-specific anthocyanin production encodes a protein sinlar to anthocyanin transciptional activators and contains the myc-homology region *Proc. Nat'l. Acad. Sci. (USA)* 86:7092 (1989).

Mangan, J. L. 1988. Nutritional effects of tannins in animal feeds. Nutr. Res. Rev. 1: 209-231.

Mabry, T. J., Markham, K. R. and Thomas, M. B. 1970. The systematic identification of flavonoids. Springer-Verlag, New York.

McKersie B D, Chen Y, de Beus M, Bowley S R, Bowler C, Inze D, D'Halluin K, Botterman J.

Superoxide dismutase enhances tolerance of freezing stress in transgenic alfalfa (*Medicago sativa* L.) Plant Physiol. 103:1155-63 (1993).

McNabb, W. C., Waghorn, G. C., Barry, T. N. and Shelton, I. D. 1993. The effect of condensed tannins in *Lotus pedunculatus* on the digestion and metabolism of methionine, cystine and inorganic sulphur in sheep. Brit J. Nutrition 70: 647-661.

Min, B. R.; Bany, T. N.; McNabb, W. C.; Kamp, P. D. Effect of condensed tannins on the production of wool and on its processing characteristics in sheep grazing *Lotus corniculatus. Aust. J. Agric. Res.* 49:597 (1998).

Muir, A. D. 1997. Antioxidative activity of condensed tannins. In: Shahdid F. Natural Antioxidants. Chemistry, Health Effects, and Applications. AOCS Press, Champaign, Ill. pp. 204-212.

Muir, A. D., Gruber, M. Y., Hinks, C. F., Lees, G. L. Onyilagha, J., Hallet, R., Xia, F., Soroka, J. and Erlandson, M. 1999. The effect of condensed tannin in the diets of major crop insects. Book chapter. In: Gross, G. G., Hemingway, R. and Yoshida, T. (Eds.) Plant Polyphenols 2: Chemistry, Biology, Pharmacology, Ecology. Plenum Press, New York. pp. 867-882.

Naczk and Shahidi, 1992. Phenolic constituents of rapeseed. In: Hemingway, R. W.; Laks, P. E. (eds.) Plant Polyphenols: Synthesis, Properties, Significance. Plenum Press, New York. pp. 895-910.

Newman, R. K.; Newman, C. W.; El-Negoumy, A. M.; Aastrup, S. Nutritive quality of proanthocyanidin-free barley. *Nutition Reports Int'l*. 30:809 (1984).

Niezen, K. E.; Waghom, T. S.; Charleston, W. A. G.; Waghorn, G. C. Growth and gastrointestinal nematode parasitism in lambs gazing either lucerne (*Medicago sativa*) or sulla (*Hedysarum coronarium*) which contains condensed tannins. *J. Agric. Sci. (Cambridge)* 125:81(1995).

Olah, A. F. and Sherwood, R. T. 1971. Phytopathology 61: 65-69.

Olson, O.; Wang, X.; von Wettstein, D. Sodium azide mutagenesis: Preferential generation of A:T-G:C transitions in the barley *Ant*18 gene. *Proc. Nat'l. Acad. Sci. USA* 90:8043 (1993).

Outtrup, H. 1992. Proanthocyanidins, the brewing process, and the quality of beer. In: Hemingway, R. W.; Laks, P. E. (eds.) Plant Polyphenols: Synthesis, Properties, Significance. Basic Life Sciences vol: 59. Plenum Press, New York pp. 849-858.

Paz-Arez, J.; Ghosal, D.; Weinard, U.; Peterson, P.; Saedler, H. The regulatory C1 locus of *Zea mays* encodes a protein with homology to myb proto-oncogene products and with structural similarities to transcriptional activators. *EMBO J.* 6:3553 (1987).

Petersen, M., Strack, D. and Matem, U. 1999. Biosynthesis of phenylpropanoid and related compounds. In: Wink M. (Ed) Biochemistry of plant secondary metabolism. Annual Plant Reviews 2: 151-221.

Polya, G. M. and Foo, L. Y. 1994. Inhibition of eukaryote signal-regulated protein kinases by plant-derived catechin-related compounds. Phytochem. 35: 1399-1405.

Porter, L. J. Flavans and proanthocyanidins. In: Harborne, J. B. (ed.) The Flavonoids. Advances in Research Since 1980. Chapman and Hall, New York. pp. 21 (1988).

Reddy, V. S.; Dash, S.; Reddy, A. R. Anthocyanin pathway in rice (*Orza sativa* L.): identification of a mutant showing dominant inhibition of anthocyanins in leaf and accumulation of proanthocyanidins in pericarp. *Theor. Appl. Genet.* 91:301 (1995).

Reed, J. D. 1987. Phenolics, fiber, and fiber digestibility in bird resistant and non-bird resistant sorghum grain. J. Agric. Food Chem. 35: 461-464.

Saleh, N. A. M, Boulos, L., El-Negoumy, S. I. and Abdalla, M. F. 1982. Biochem. Syst. Ecol. 10: 33-36.

Sambrook et al. (1989). Molecular Cloning: A Laboratory Manual, Cold Spring Harbor Laboratory Press, Cold Spring Harbor. N.Y.

Simbaya, J., Slominski, B. A., Rakow, G., Campbell, L. D., Downey, R. K. and Bell, J. M. 1995. Quality characteristics of yellow-seeded Brassica seed meals: Protein, carbohydrates and dietary fiber components. J. Agric. Food Chem. 43: 2062-2066.

Singh, S.; McCallum, J.; Gruber, M. Y.; Towers, G. H. N.; Muir, A. D.; Bohm, B. A.; Koupai-Abazani, M. R.; Glass, A. D. M. Biosynthesis of flavan-3-ols by leaf extracts of Onobrychis viciifolia. Phytochemistry 44:425 (1997).

Singleton, V. L. 1992. Tannins and the qualities of wine. In: Hemingway, R. W.; Laks, P. E. (eds.) Plant Polyphenols: Synthesis, Properties, Significance. Basic Life Sciences vol. 59. Plenum Press, New York. pp. 859-880.

Skadhauge, B. Genetics and biochemistry of proanthoeyanidin biosynthesis and their biological significance in crop plants. PhD thesis. The Royal Veterinary and Agriculture University, Copenhagen, Demnark (1996).

Skadhauge, B.; Gruber, M. Y.; Thomsen, K. K.; von Wetftein, D. Leucocyanidin reductase activity and accumulation of proanthocyanidins in developing legume tissue. Am. J. Botany 84:494 (1997a).

Skadhauge, B.; Thomsen, K. K.; von Wettstein, D. The role of the barley testa layer and its flavonoid content in resistance to Fusarium infections. Hereditas 126:147 (1997b).

Tanner, G. J.; Moate, P.; Dailey, L.; Laby, R.; Larkin, P. J. Proanthocyanidins (condensed tannins) destebilise plant protein foams in a dose dependent manner. Aust. J. Agric. Res. 46:1011 (1995).

Tanner, G. J.; Moore, A. E.; Larkin, P. J. Proanthocyanidins inhibit hydrolysis of leaf proteins by rumen microflora in vitro. Brit. J. Nutr. 71: 47 (1994).

Treutter, D. and Feucht, W. 1990. The pattern of flavan-3-ols in relation to scab resistance of apple cultivars. J. Hort. Sci. 65: 511-517.

Von Wettstein, D.; Jende-Strid, B.; Alirenst-Larsen, B.; Sorensen, J. A. Biochemical mutant in barley renders chemical stabilization of beer superfluous. Carlsberg Res. Commun. 42:341 (1979).

Von Wettstein, D. and Hagie, F. 1998. WO98/59056.

Waghom, G. C., Reed, J. D. and Ndlovu, L. R. 1999. Condensed tannins and herbivore nutrition Abstracts. Proc. Grasslands 2000. XVIII Int'l Grasslands Congress. Winnipeg/Saskatoon, Canada 1997. Vol. 31, Session 8.

Wang, X.; Olsen, O.; Knudsen, S. Expression of the dihydroflavonol reductase gene in an anthocyanin-free barley mutant. Hereditas 119:67 (1993).

Wong, J. R.; Walker, L. S.; Drikeilis, H.; Klein, T. M. Anthocyanin regulatory genes from maize B-Peru and C1 activate the anthocyanin pathway in wheat, barley and oat cells. J. Cell Biochem. Suppl. 0(15 part A):159 (1991).

Zhang, J., Takahashi, K, Kono, Y., Suzuki, Y., Takeuchi, S., Shimizu, T., Yamaguchi, I., Chijimatsu, M., Sakurai, A., Sato, Y. and Kitamura, H. 1990. Bioactive condensed tannins from bark: Chemical properties, enzyne inhibition and anti-plant-viral activities. J. Pesticide Sci. 15: 585-591

TABLE 1

Phenylpropanoid/flavonoid pathway illustrating the formation of flavonoids, anthocyanins and condensed tannins.

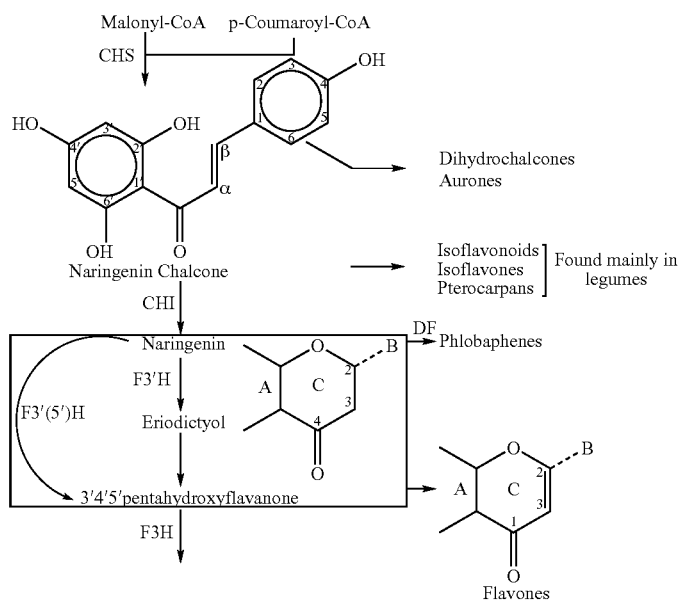

TABLE 1-continued

Phenylpropanoid/flavonoid pathway illustrating the formation of flavonoids, anthocyanins and condensed tannins.

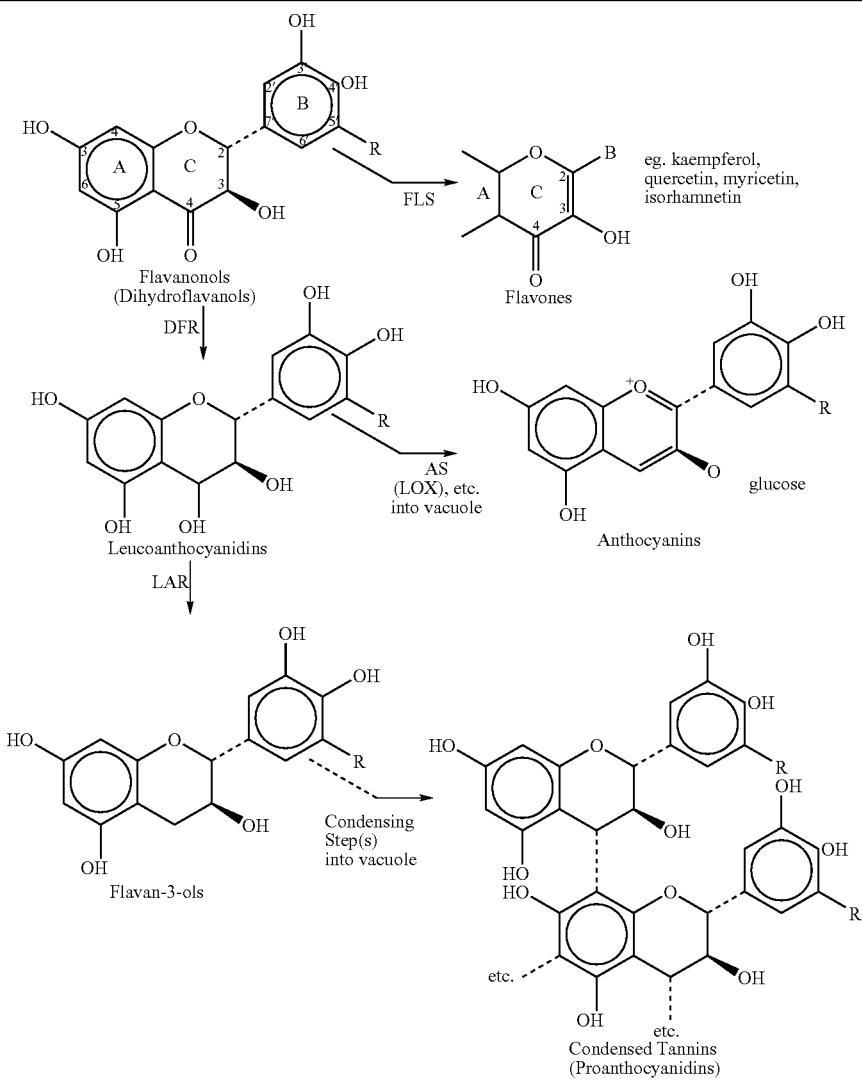

TABLE 2

Comparision of transgenic Lc-alfalfa genotypes with different transgene sizes

| Characteristics | Number of transgenic alfalfa genotypes | |
| --- | --- | --- |
| Size of Lc transgene | 2.4 kb | 2.2 kb |
| Lc expressed under mild greenhouse conditions | 6 | 6 |
| Red leaves when forming roots from cuttings under mild greenhouse conditions | 4 (dark red) out of 6 Lc-expressing genotypes | 2 (light red) out of 6 Lc-expressing genotypes |
| Red leaf/stem phenotype in response to cold exposure | 1 out of 1 Lc-expressing genotype tested | 4 out of 4 Lc-expressing genotypes tested |
| | Days | Number of Lc-expressing alfalfa genotypes | |
| Red leaf/stem phenotype in response to 1-4 days of exposure to natural daylight | 1 | 4 | 0 |
| | 2 | 1 | 1 |
| | 3 | | 2 |
| | 4 | | |
| No response to daylight | | 1 | 3 |

TABLE 3

Relative induction of flavonoid genes in Lc-alfalfa genotype 88-19 (2.4 kb Lc) after exposure to cold.

| | Relative Gene Expression* | | |
|---|---|---|---|
| Gene Probe | 20° C./400 uE | 4° C./40 uE | 4° C./200 uE |
| Lc | 1.0 | 3.3 | 8.7 |
| CHS | 1.0 | 0.6 | 1.2 |
| F3H | 1.0 | 4.4 | 4.6 |
| Plant phenotype | green | green | Dark red-green |

*NB: For relative quantification, radioactivity on the Northern blot in FIG. 2, panel B was normalized to the amount of two major rRNA bands loaded on each gel lane, then expressed as a ratio of the 20° C. RNA sample. The same type of induction pattern was also found with normalization relative to a *Brassica napus* actin probe.

TABLE 4

Comparison of transgenic Lc-alfalfa genotypes grown in a field trial in 2001 under Canadian prairie conditions. Part I. Anthocyanin induction and gene expression.

| Plant Family (Lc transgene size) | Plant # | Field colour | Anthocyanin content (relative to parent) | Lc RNA | CHS RNA |
|---|---|---|---|---|---|
| 88 (2.4 kb) | 1 | deep red | 25X | 6.15 | 1.56 |
| | 4 | deep red | 15X | 1.83 | 1.35 |
| | 7 | green | 3X | 0.00 | 0.28 |
| | 9 | deep red | n.d. | 6.48 | 0.70 |
| | 19 | deep red | 17X | 3.24 | 0.76 |
| 90 (2.2 kb) | 1 | green | 1X | 0.00 | 0.12 |
| | 5a | red | 8X | 2.08 | 0.10 |
| | 13 | green | 2X | 0.00 | 0.15 |
| | 19 | red | 9X | 3.31 | 0.37 |
| | 39 | red | 12X | 2.33 | 0.15 |
| Non-transformed | A01 (parent) | green | 1X | n.d. | n.d. |
| | A04 | green | n.d. | 0.00 | 0.44 |

*lines 88-1 to 88-19 have 2.4 Kb Lc construct lines 90-1 to 90-39 have 2.2 Kb Lc construct.
Lines A01, A04 are non-transformed controls.
n.d. indicates not determined.
Anthocyanin was measured following mild acid hydrolysis and centrifugation of extract, at 523 nm.
RNA was quantified using densitometry scans of Northern blots probed with indicated genes.

TABLE 5

Relative amounts of luteolin and apigenin flavones in Lc-transgenic and non-transgenic alfalfa

| | Stems | | Leaves | |
|---|---|---|---|---|
| Genotype | Luteolin | Apigenin | Luteolin | Apigenin |
| A01 | 100 | 100 | 100 | 100 |
| 88-4 | 8 | 100 | 41 | 120 |
| 88-19 | 33 | 80 | 44 | 24 |
| 90-19 | 9 | 91 | 17 | 47 |

NB: The data for each plant is based on the same weight of plant material used to develop the extracts. The HPLC UV-detector response for luteolin and apigenin peaks in the A01 non-transformed parent was normalized to 100. Data for the transgenic plant peaks was expressed proportionately to the A01 peaks.

TABLE 6

Ratio of luteolin to apigenin in Lc-transgenic and non-transgenic alfalfa

| | Stems | | Leaves | |
|---|---|---|---|---|
| Genotype | Luteolin | Apigenin | Luteolin | Apigenin |
| A01 | 100 | 59 | 100 | 264 |
| 88-4 | 100 | 711 | 100 | 800 |
| 88-19 | 100 | 137 | 100 | 139 |
| 90-19 | 100 | 567 | 100 | 276 |

NB: The data for each plant is based on the same weight of plant material used to develop the extracts. The HPLC UV-detector response for luteolin for each genotype was normalized to 100. Data for the apigenin peak in each genotype was expressed proportionately to the luteolin peak.

All publications, patents, and patent applications are incorporated by reference herein, as though individually incorporated by reference.

We claim:

1. A transgenic leguminous plant, plant tissue or plant cell comprising an expressible nucleic acid sequence encoding a Lc regulatory protein, said plant, plant tissue or plant cell exhibiting altered levels of condensed tannins, wherein said nucleic acid sequence is selected from the group consisting of:
    a) a nucleic acid encoding the Lc regulatory protein, wherein the nucleic acid comprises SEQ ID NO:1;
    b) a nucleic acid sequence sharing at least 95% sequence identity with SEQ ID NO:1;
    c) an antisense nucleic acid sequence of a) or b);
    d) a nucleic acid complementary to any one of a) to c); and
    e) a nucleic acid degeneracy equivalent to any one of a) to d).

2. The transgenic plant, plant tissue or plant cell of claim 1, wherein said nucleic acid sequence is under the control of a promoter.

3. The transgenic plant, plant tissue or plant cell of claim 2, wherein said nucleic acid sequence is under the control of a promoter selected from the group consisting of CaMV 35S promoter, nos promoter, small subunit rubisco promoter, light induced promoter, leaf specific promoter and vegetation specific promoter.

4. The transgenic plant, plant tissue or plant cell of claim 3, wherein said plant, plant tissue or plant cell is selected from the group consisting of mature plant, immature plant, leaf, stem, flower, root, seed and seedling.

5. The transgenic plant, plant tissue or plant cell of claim 4, wherein said plant, plant tissue or plant cell is selected from the group consisting of alfalfa, white clover, red clover, alsike clover, sweetclover and subterranean clover.

6. The transgenic plant, plant tissue or plant cell of claim 1, wherein said plant, plant tissue or plant cell is an alfalfa plant, plant tissue or plant cell.

7. The transgenic alfalfa plant of claim 6, wherein said nucleic acid sequence is under the control of a suitable promoter.

8. The transgenic alfalfa plant of claim 7, wherein said nucleic acid sequence is under the control of a promoter selected from the group consisting of CaMV 35S promoter, nos promoter, small subunit rubisco promoter, light induced promoter, leaf specific promoter and vegetation specific promoter.

9. The transgenic alfalfa plant of claim 6, wherein said nucleic acid sequence expression is further induced by an environmental stress factor selected from the group consisting of light and cold temperature.

10. A method for the production of a transgenic alfalfa plant exhibiting altered expression of condensed tannins, said method comprising the step of;
 transforming an alfalfa plant with a nucleic acid sequence selected from the group consisting of;
  a) a nucleic acid comprising SEQ ID NO:1;
  b) a nucleic acid sequence sharing at least 95% sequence identity with SEQ ID NO:1;
  c) an antisense nucleic acid, sequence of a) or b);
  d) a nucleic acid complementary to any one of a) to c); and
  e) a nucleic acid degeneracy equivalent to any one of a) to d).

11. The method of claim 10, wherein said nucleic acid sequence is under the control of a CaMV promoter.

12. The method of claim 10, wherein said method further comprises the step of subjecting said plant to an environmental stress factor selected from the group consisting of light and cold temperature, wherein said stress factor further potentiates the expression of said nucleic acid sequence.

13. A method for producing a transgenic leguminous plant, plant tissue or plant cell exhibiting altered levels of condensed tannins, said method comprising the steps of;
 transforming a leguminous plant, plant tissue or plant cell with a nucleic acid sequence selected from the group consisting of;
  a) a nucleic acid comprising SEQ ID NO:1;
  b) a nucleic acid sequence sharing at least 95% sequence identity with a);
  c) an antisense nucleic acid sequence of a) or b);
  d) a nucleic acid complementary to any one of a) to c); and
  e) a nucleic acid degeneracy equivalent to any one of a) to d).

14. The method of claim 13, wherein said nucleic acid sequence is under the control of CaMV promoter.

15. A method for inducing or increasing condensed tannin synthesis in an alfalfa plant comprising:
 transforming an alfalfa plant with a nucleic acid sequence selected from the group consisting of;
  a) a nucleic acid comprising SEQ ID NO:1;
  b) a nucleic acid sequence sharing at least 95% sequence identity with a);
  c) a nucleic acid degeneracy equivalent to any one of a) to b); and
 selecting a transformed plant wherein the nucleic acid is expressed, whereby condensed tannin synthesis is induced or increased in the plant.

16. The method of claim 15, wherein said nucleic acid sequence is under the control of CaMV promoter.

17. The method of claim 15, further comprising exposing said plant to an environmental stress factor selected from the group consisting of light and cold temperature.

18. A method for regulating production of flavonols in an alfalfa plant comprising:
 transforming an alfalfa plant with an isolated nucleic acid selected from the group consisting of:
  a) a nucleic acid comprising SEQ ID NO:1;
  b) a nucleic acid sequence sharing at least 95% sequence identity with a);
  c) an antisense nucleic acid sequence of a) or b);
  d) a nucleic acid complementary to any one of a) to c); and
  e) a nucleic acid degeneracy equivalent to any one of a) to d).

19. A method to improve the forage quality of a leguminous plant, said method comprising:
 transforming a leguminous plant, plant tissue or plant cell with a nucleic acid sequence selected from the group consisting of:
  a) a nucleic acid comprising SEQ ID NO:1;
  b) a nucleic acid sequence sharing at least 95% sequence identity with a); and
  c) a nucleic acid degeneracy equivalent to any one of a) to b);
 wherein expression of said nucleic acid alters levels of condensed tannins in the plant.

20. The method of claim 19, wherein said nucleic acid sequence is under the control of a promoter.

* * * * *

SEQUENCE LISTING

<160> NUMBER OF SEQ ID NOS: 2

<210> SEQ ID NO 1
<211> LENGTH: 2605
<212> TYPE: DNA
<213> ORGANISM: Maize

<400> SEQUENCE: 1

| | | | | | |
|---|---|---|---|---|---:|
| cccaaggttc | gtggcatatc | tgtaggcatc | tacccgtct | tcgtcgtccg | ctcctcacta | 60 |
| gctaccaaga | ggtcgccatt | attgccaaca | tagagtgtac | gtggatgtct | atatatatgc | 120 |
| ctacttgcac | ccatatggca | taggcgttcg | atccccttag | cgcggaggag | agctcctccg | 180 |
| gttcttctct | acccttcgca | tggaagttct | tgcattgctt | cgttgcttct | ctagtttctt | 240 |
| ccttctacgt | ctttccagca | tacgcatgcc | cctcgtccgc | cggttcacga | ggcatcgtct | 300 |
| gatgatcagt | agataataag | caatataata | ctgatctaga | atcgagttgt | tgtactcttc | 360 |
| gcagataggc | gcgtgatggc | gctttcagct | tcccgagttc | agcaggcgga | agaactgctg | 420 |
| caacgacctg | ctgagaggca | gctgatgagg | agccagcttg | ctgcagccgc | caggagcatc | 480 |
| aactggagct | acgccctctt | ctggtccatt | tcagacactc | aaccaggggt | gctgacgtgg | 540 |
| acggacgggt | tctacaacgg | cgaggtgaag | acgcggaaga | tctccaactc | cgtggagctg | 600 |
| acatccgacc | agctcgtcat | gcagaggagc | gaccagctcc | gggagctcta | cgaggccctc | 660 |
| ctgtcgggcg | agggcgaccg | ccgcgctgcg | cctgcgcggc | cggccggctc | tctgtcgccg | 720 |
| gaggacctcg | gcgacaccga | gtggtactac | gtggtctcca | tgacctacgc | cttccggcca | 780 |
| ggccaagggt | tgcccggcag | gagtttcgcg | agcgacgagc | atgtctggct | gtgcaacgcg | 840 |
| cacctcgccg | gcagcaaagc | cttcccccgc | gcgctcctgg | ccaagagcgc | gtccattcag | 900 |
| tcaatcctct | gcatcccggt | tatgggcggc | gtgcttgagc | ttggtacaac | tgacacggtg | 960 |
| ccggaggccc | cggacttggt | cagccgagca | accgcggctt | tctgggagcc | gcagtgcccg | 1020 |
| agctccagcc | cgtcaggacg | agcaaacgag | accggcgagg | ccgcagcaga | cgacggcacg | 1080 |
| tttgcgttcg | aggaactcga | ccacaataat | ggcatggacg | acatagaggc | gatgaccgcc | 1140 |
| gccgggggac | acgggcagga | ggaggagcta | agactaagag | aagccgaggc | cctgtcagac | 1200 |
| gacgcaagcc | tggagcacat | caccaaggag | atcgaggagt | tctacagcct | ctgcgacgaa | 1260 |
| atggacctgc | aggcgctacc | actaccgcta | gaggacggct | ggaccgtgga | cgcgtccaat | 1320 |
| ttcgaggtcc | cctgctcttc | cccgcagcca | gcgccgcctc | cggtggacag | ggctaccgct | 1380 |
| aacgtcgccg | ccgacgcctc | aagggcaccc | gtctacggct | ctcgcgcgac | gagtttcatg | 1440 |
| gcttggacga | ggtcctcgca | gcagtcgtcg | tgctccgacg | acgcggcgcc | cgcagcagta | 1500 |
| gtgccggcca | tcgaggagcc | gcagagattg | ctgaagaaag | tggtggccgg | cggcggtgct | 1560 |
| tgggagagct | gtgcggcgc | gacgggagca | gcacaggaaa | tgagtggcac | tggcaccaag | 1620 |
| aaccacgtca | tgtcggagcg | aaagcgacga | gagaagctca | acgagatgtt | cctcgtcctc | 1680 |
| aagtcactgc | ttccgtccat | tcacagggtg | aacaaagcgt | cgatcctcgc | cgaaacgata | 1740 |
| gcctacctca | aggagcttca | gagaagggtg | caagagctgg | agtccagtag | ggaacctgcg | 1800 |
| tcgcgcccat | ccgaaacgac | gacaaggcta | ataacaaggc | cctcccgtgg | caataatgag | 1860 |
| agtgtgagga | aggaggtctg | cgcgggctcc | aagaggaaga | gcccagagct | cggcagagac | 1920 |
| gacgtggagc | gcccccgggt | cctcaccatg | gacgccggca | ccagcaacgt | caccgtcacc | 1980 |
| gtctcggaca | aggacgtgct | cctggaggtg | cagtgccggt | gggaggagct | cctgatgacg | 2040 |

```
cgagtgttcg acgccatcaa gagcctccat ttggacgtcc tctcggttca ggcttcagcg    2100
ccagatggct tcatggggct taagatacga gctcagtttg ctggctccgg tgccgtcgtg    2160
ccctggatga tcagcgaggc tcttcgcaaa gctataggga agcggtgaag gggcagctgg    2220
aaatttggac atcgacgggc atggaaggct tcatgggatc gaagcaaaga tgtatttctt    2280
gtttctttag ataacagaca tgaatcggac ctttatatca acaattatat gggcatgaat    2340
acttaagact ccagccctta acacgtagaa actcaaaaaa gaagagagga agctaaagac    2400
taagcgtaag gtatatttgg aagtaaaatta tttttatagt ttctaagcaa tctcatggtt    2460
tataggaata ctagagtgtt tatggcataa ggtgtttggt tgcattcata aaacctatat    2520
tttcaaagtc atagcattct agataccatg atatttttgt aatattggaa actacactcc    2580
aacgcaaagt ttttatgaca tggct                                          2605
```

<210> SEQ ID NO 2
<211> LENGTH: 610
<212> TYPE: PRT
<213> ORGANISM: Maize

<400> SEQUENCE: 2

```
Met Ala Leu Ser Ala Ser Arg Val Gln Gln Ala Glu Glu Leu Leu Gln
 1               5                  10                  15

Arg Pro Ala Glu Arg Gln Leu Met Arg Ser Gln Leu Ala Ala Ala Ala
             20                  25                  30

Arg Ser Ile Asn Trp Ser Tyr Ala Leu Phe Trp Ser Ile Ser Asp Thr
         35                  40                  45

Gln Pro Gly Val Leu Thr Trp Thr Asp Gly Phe Tyr Asn Gly Glu Val
     50                  55                  60

Lys Thr Arg Lys Ile Ser Asn Ser Val Glu Leu Thr Ser Asp Gln Leu
 65                  70                  75                  80

Val Met Gln Arg Ser Asp Gln Leu Arg Glu Leu Tyr Glu Ala Leu Leu
                 85                  90                  95

Ser Gly Glu Gly Asp Arg Arg Ala Ala Pro Ala Arg Pro Ala Gly Ser
            100                 105                 110

Leu Ser Pro Glu Asp Leu Gly Asp Thr Glu Trp Tyr Tyr Val Val Ser
        115                 120                 125

Met Thr Tyr Ala Phe Arg Pro Gly Gln Gly Leu Pro Gly Arg Ser Phe
    130                 135                 140

Ala Ser Asp Glu His Val Trp Leu Cys Asn Ala His Leu Ala Gly Ser
145                 150                 155                 160

Lys Ala Phe Pro Arg Ala Leu Leu Ala Lys Ser Ala Ser Ile Gln Ser
                165                 170                 175

Ile Leu Cys Ile Pro Val Met Gly Gly Val Leu Glu Leu Gly Thr Thr
            180                 185                 190

Asp Thr Val Pro Glu Ala Pro Asp Leu Val Ser Arg Ala Thr Ala Ala
        195                 200                 205

Phe Trp Glu Pro Gln Cys Pro Ser Ser Pro Ser Gly Arg Ala Asn
    210                 215                 220

Glu Thr Gly Glu Ala Ala Ala Asp Asp Gly Thr Phe Ala Phe Glu Glu
225                 230                 235                 240

Leu Asp His Asn Asn Gly Met Asp Asp Ile Glu Ala Met Thr Ala Ala
                245                 250                 255

Gly Gly His Gly Gln Glu Glu Leu Arg Leu Arg Glu Ala Glu Ala
            260                 265                 270
```

-continued

```
Leu Ser Asp Asp Ala Ser Leu Glu His Ile Thr Lys Glu Ile Glu Glu
            275                 280                 285

Phe Tyr Ser Leu Cys Asp Glu Met Asp Leu Gln Ala Leu Pro Leu Pro
        290                 295                 300

Leu Glu Asp Gly Trp Thr Val Asp Ala Ser Asn Phe Glu Val Pro Cys
305                 310                 315                 320

Ser Ser Pro Gln Pro Ala Pro Pro Val Asp Arg Ala Thr Ala Asn
                325                 330                 335

Val Ala Ala Asp Ala Ser Arg Ala Pro Val Tyr Gly Ser Arg Ala Thr
            340                 345                 350

Ser Phe Met Ala Trp Thr Arg Ser Ser Gln Gln Ser Ser Cys Ser Asp
            355                 360                 365

Asp Ala Ala Pro Ala Ala Val Val Pro Ala Ile Glu Glu Pro Gln Arg
            370                 375                 380

Leu Leu Lys Lys Val Val Ala Gly Gly Ala Trp Glu Ser Cys Gly
385                 390                 395                 400

Gly Ala Thr Gly Ala Ala Gln Glu Met Ser Gly Thr Gly Thr Lys Asn
                405                 410                 415

His Val Met Ser Glu Arg Lys Arg Arg Glu Lys Leu Asn Glu Met Phe
            420                 425                 430

Leu Val Leu Lys Ser Leu Leu Pro Ser Ile His Arg Val Asn Lys Ala
            435                 440                 445

Ser Ile Leu Ala Glu Thr Ile Ala Tyr Leu Lys Glu Leu Gln Arg Arg
    450                 455                 460

Val Gln Glu Leu Glu Ser Ser Arg Glu Pro Ala Ser Arg Pro Ser Glu
465                 470                 475                 480

Thr Thr Thr Arg Leu Ile Thr Arg Pro Ser Arg Gly Asn Asn Glu Ser
                485                 490                 495

Val Arg Lys Glu Val Cys Ala Gly Ser Lys Arg Lys Ser Pro Glu Leu
            500                 505                 510

Gly Arg Asp Asp Val Glu Arg Pro Pro Val Leu Thr Met Asp Ala Gly
            515                 520                 525

Thr Ser Asn Val Thr Val Thr Val Ser Asp Lys Asp Val Leu Leu Glu
    530                 535                 540

Val Gln Cys Arg Trp Glu Glu Leu Leu Met Thr Arg Val Phe Asp Ala
545                 550                 555                 560

Ile Lys Ser Leu His Leu Asp Val Leu Ser Val Gln Ala Ser Ala Pro
                565                 570                 575

Asp Gly Phe Met Gly Leu Lys Ile Arg Ala Gln Phe Ala Gly Ser Gly
            580                 585                 590

Ala Val Val Pro Trp Met Ile Ser Glu Ala Leu Arg Lys Ala Ile Gly
            595                 600                 605

Lys Arg
    610
```